United States Patent [19]

Mertens et al.

[11] Patent Number: 5,116,843
[45] Date of Patent: May 26, 1992

[54] TRICYCLIC BENZIMIDAZOLE COMPOUNDS, PHARMACEUTICAL COMPOSITIONS AND METHODS OF USE

[75] Inventors: Alfred Mertens, Schriesheim; Wolfgang von der Saal, Weinhim; Erwin Boehm, Ladenburg; Klaus Strein, Hemsbach, all of Fed. Rep. of Germany

[73] Assignee: Boehringer Mannheim GmbH, Mannheim, Fed. Rep. of Germany

[21] Appl. No.: 543,350

[22] Filed: Jun. 25, 1990

Related U.S. Application Data

[62] Division of Ser. No. 144,514, Jan. 15, 1988, Pat. No. 4,954,498.

[30] Foreign Application Priority Data

Jan. 17, 1987 [DE] Fed. Rep. of Germany ....... 3701277

[51] Int. Cl.$^5$ ................ A61K 31/495; A61K 31/415; C07D 237/00; C07D 471/02
[52] U.S. Cl. .................... 514/253; 514/254; 514/267; 514/293; 544/98; 544/182; 544/224; 544/238; 544/242; 544/251; 544/358; 544/360; 546/82
[58] Field of Search ............... 546/82; 514/293, 267, 514/253, 254; 544/224, 238, 98, 182, 358, 360, 242, 251

[56] References Cited

PUBLICATIONS

Chemical Abstracts, 84:90072m Structure-activity relations of histamine analogs, 12. Imidazo [4.5-g] quinolines Lebenstedt et al. (1976).

*Primary Examiner*—Mary C. Lee
*Assistant Examiner*—Joseph K. McKane
*Attorney, Agent, or Firm*—Felfe & Lynch

[57] ABSTRACT

The present invention provides tricyclic benzimidazoles of the formula

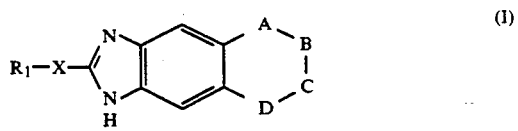

(I)

wherein $R_1$ is a phenyl radical of the general formula:

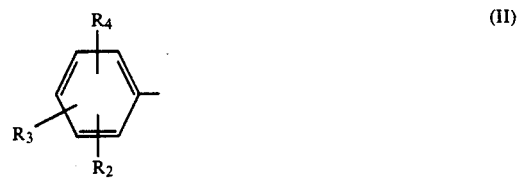

(II)

wherein $R_2$, $R_3$ and $R_4$ can be the same or different as in claim 1. For A, B, C and D are understood those compounds where one or two of A, B, C or D are nitrogen. These compounds are useful to inhibit the aggregation of thrombocytes and erythrocytes, lower blood pressure and can increase the power of the heart.

27 Claims, No Drawings

TRICYCLIC BENZIMIDAZOLE COMPOUNDS, PHARMACEUTICAL COMPOSITIONS AND METHODS OF USE

This is a divisional application of application Ser. No. 144,514, filed Jan. 15, 1988, now U.S. Pat. No. 4,954,498.

The is concerned with new tricyclic benzimidazoles, with processes for the preparation thereof and with pharmaceutical compositions containing them.

The new tricyclic benzimidazoles of the present invention are compounds of the general formula:

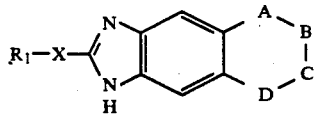 (I)

wherein $R_1$ is a phenyl radical of the general formula:

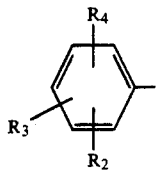 (II)

wherein $R_2$, $R_3$ and $R_4$ can be the same or different and each is a hydrogen atom, an alkanesulphonyloxy, trifluoromethanesulphonyloxy, alkanesulphonylamino, trifluoromethanesulphonylamino, N-alkyl-alkanesulphonylamino, N-alkyltrifluoromethanesulphonylamino, alkylsulphenylmethyl, alkylsulphinylmethyl or alkylsulphonylmethyl radical, a carbonyl group substituted by hydroxyl, alkoxy, amino, alkylamino or dialkylamino, a sulphonyl group substituted by amino, alkylamino, dialkylamino or cyclic imino, whereby a methylene group can be replaced by a sulphur or oxygen atom, an alkylcarbonylamino, aminocarbonylamino, alkylaminocarbonylamino, alkylthio, alkylsulphinyl or alkylsulphonyl radical, a nitro group, a halogen atom, an amino or hydroxyl group, an alkyl, alkoxy, alkenyloxy, alkynyloxy, cyanoalkoxy, carboxyalkoxy, alkoxycarbonylalkoxy, hydroxyalkyl, dialkylamino, 1-imidazolyl or trifluoromethyl radical, a cyano group or a hydroxysulphonyl, bis-(hydroxyalkyl)-amino, 1-pyrrolidino, 1-piperidino, 4-morpholino, 4-thiomorpholino, 1-pyrazolyl, 1-triazolyl, 2-oxopyrrolidinyl, 2-oxopiperidine or pyrrolyl radical or $R_1$ is a naphthyl or methylenedioxyphenyl radical or a saturated or unsaturated heterocyclic five-membered ring with 1 to 4 heteroatoms or a heterocyclic six-membered ring with 1 to 5 heteroatoms, the heteroatoms of which can be the same or different and can be oxygen, sulphur or nitrogen and, if desired, can carry an oxygen atom on one or more nitrogen atoms and the five- and six-membered rings are optionally substituted one or more times by alkyl, alkoxy, alkylthio, hydroxyl, oxo, nitro, amino, halogen or cyano and optionally condensed with a phenyl ring to form a bicyclic radical or, when X is a valency bond, besides the above-mentioned groups, $R_1$ can also be a hydrogen atom, an alkyl, cycloalkyl, alkenyl, cycloalkenyl, alkynyl, haloalkyl, alkoxyalkyl, carboxyalkyl, alkoxycarbonylalkyl, aminoalkyl, hydroxyalkyl, hydroxyl, mercapto, amino, alkylthio, alkylcarbonylamino, formylamino, alkylsulphonylamino, formylaminoalkyl, alkoxycarbonylaminoalkyl, alkylsulphonylaminoalkyl, alkylcarbonylamino, trifluoromethyl or alkylcarbonylaminoalkyl radical, X is a valency bond, an alkylene or vinylene radical, an imino group (—NH—) or an amide group (—CONH—) and A, B, C and D, independently of one another, are carbon and nitrogen atoms which can be substituted by hydrogen atoms or alkyl or cycloalkyl radicals, whereby the carbon atoms can also carry hydroxyl or oxo groups or can be components of a 3 to 7 membered spirocycle, whereby the six-membered ring containing A, B, C and D can be saturated, partly unsaturated or unsaturated, the tautomers thereof and the physiologically acceptable salts thereof with inorganic and organic acids.

When the compounds of general formula I contain an asymmetric carbon atom, the optically-active compounds and racemic mixtures are also the subject of the present invention.

The new compounds of general formula I possess valuable pharmacological properties. In particular, they inhibit the aggregation of thrombocytes and erythrocytes and/or lower the blood pressure and/or can increase the heart power.

When $R_1$ is a phenyl radical of general formula II, then the alkyl moiety of the substituents mentioned in the case of $R_2$, $R_3$ and $R_4$ can contain up to 5 carbon atoms and preferably up to 4 carbon atoms, the alkyl moiety being straight-chained or branched. Preferred in this sense are, for example, the methanesulphonyloxy, ethanesulphonyloxy, n-propanesulphonyloxy, iso-propanesulphonyloxy, trifluoromethanesulphonyloxy, methylsulphenylmethyl, ethylsulphenylmethyl, n-propylsulphenylmethyl, methylsulphinylmethyl, ethylsulphinylmethyl, methylsulphonylmethyl, ethylsulphonylmethyl, n-propylsulphonylmethyl, methanesulphonylamino, ethanesulphonylamino, n-propanesulphonylamino, trifluoromethanesulphonylamino, N-methyl-methanesulphonylamino, N-ethylmethanesulphonylamino, N-methyl-ethanesulphonylamino, N-isopropylethanesulphonylamino, N-methyl-n-propanesulphonylamino, N-n-propyl-n-propanesulphonylamino, N-methyl-trifluoromethanesulphonylamino, N-ethyl-trifluoromethanesulphonylamino, N-isopropyl-trifluoromethanesulphonylamino, methoxycarbonyl, ethoxycarbonyl, propoxycarbonyl, isopropoxycarbonyl, methylaminocarbonyl, ethylaminocarbonyl, dimethylaminocarbonyl, di-(n-propylamino)-carbonyl, N-methyl-ethylaminocarbonyl, trifluoromethyl, methylaminosulphonyl, ethylaminosulphonyl, n-propylaminosulphonyl, n-butylaminosulphonyl, n-pentylaminosulphonyl, dimethylaminosulphonyl, diethylaminosulphonyl, di-n-(propylamino)-sulphonyl, N-methyl-isopropylaminosulphonyl, acetylamino, propionylamino, methylaminocarbonylamino, ethylaminocarbonylamino, propylaminocarbonylamino, a methyl, ethyl, propyl, methoxy, ethoxy, propyloxy, allyloxy, but-2-enyloxy, but-3-enyloxy, pent-2-enyloxy, propargyloxy, but-2-ynyloxy, but-3-ynyloxy, cyanomethoxy, cyanoethoxy, methoxycarbonylmethoxy, methoxycarbonylethoxy, hydroxymethyl, methylthio, ethylthio, methylsulphinyl, ethylsulphinyl, methylsulphonyl or ethylsulphonyl radical.

In the case of sulphonyl groups which can be substituted by cyclic imino groups, the morpholino-, pyrrolidino-, piperidino- and hexamethyleneiminosulphonyl radicals are preferred.

$R_2$ is especially preferably a hydrogen atom or an alkylsulphonyloxy, trifluoromethylsulphonyloxy, alkylsulphenylmethyl, alkylsulphinylmethyl, alkylsulphonylmethyl, alkylsulphonylamino, N-alkyl-alkylsulphonylamino, trifluoromethylsulphonylamino or N-alkyl-trifluoromethylsulphonylamino radical, a carbonyl group substituted by hydroxyl, alkoxy, amino, alkylamino or dialkylamino or a sulphonyl group substituted by amino, dialkylamino or morpholino, each of the above-mentioned alkyl moieties containing 1 or 2 carbon atoms, a nitro or cyano group or an alkylaminosulphonyl group containing up to 4 carbon atoms, an alkylcarbonylamino, aminocarbonylamino, N-alkylaminocarbonylamino, alkylthio, alkylsulphinyl or alkylsulphonyl radical, each of the above-mentioned alkyl moieties containing 1 or 2 carbon atoms, a halogen atom, an amino or hydroxyl group, a dialkylamino, alkyl, alkoxy, alkenyloxy or alkynyloxy group preferably containing up to 3 carbon atoms, a cyanomethoxy, methoxycarbonylmethoxy, trifluoromethyl or 1-imidazolyl radical, $R_3$ is especially preferably a hydrogen atom, an alkyl radical containing up to 3 carbon atoms, an alkoxy radical or a dialkylamino radical containing 1 or 2 carbon atoms in each alkyl moiety or a halogen atom and $R_4$ is especially preferably a hydrogen atom or a methoxy radical.

The phenyl moiety can carry 1 to 3 of these substituents.

Preferred monosubstituted phenyl radicals include hydroxy-, $C_1-C_3$-alkyl-, $C_1-C_3$-alkoxy, allyloxy-, propargyloxy-, cyanomethoxy-, methoxycarbonylmethoxy-, halo-, nitro-, cyano-, aminocarbonyl-, methoxycarbonyl-, amino-, $C_1-C_3$-dialkylamino-, $C_1-C_3$-alkylthio-, $C_1-C_3$-alkylsulphinyl-, $C_1-C_3$-alkylsulphonyl-, $C_1-C_3$-alkyl-sulphonyloxy- and 1-imidazolyl-phenyls, the substituents being in the 2-, 3- or 4-position.

Preferred disubstituted phenyl radicals contain, as substituents, alkanesulphonyloxy, trifluoromethylsulphonyloxy, alkylsulphenylmethyl, alkylsulphinylmethyl, alkylsulphonylmethyl, alkylsulphonylamino, N-alkylalkylsulphonylamino, trifluoromethylsulphonylamino or N-alkyl-trifluoromethylsulphonylamino radicals, carbonyl groups substituted by hydroxyl, alkoxy, amino, alkylamino or dialkylamino or sulphonyl groups substituted by amino, dialkylamino or morpholino, alkylaminosulphonyl, alkylcarbonylamino, aminocarbonylamino or N-alkylaminocarbonylamino radicals, hydroxyl groups, alkyl, alkoxy, allyloxy, propargyloxy, cyanomethoxy, methoxycarbonylmethoxy, cyano, halo, nitro, amino, dialkylamino, alkylthio, alkylsulphinyl, alkylsulphonyl or 1-imidazolyl groups, the two substituents being the same or different and being in the 2,3-, 2,4-, 2,5-, 2,6-, 3,4- or 3,5-position but preferably in the 2,4-, 2,5- or 3,4-position and the above-mentioned alkyl moieties, alone or in combination with other radicals, can contain up to 3 carbon atoms.

The preferred trisubstituted phenyl radical is the 3,4,5-trimethoxyphenyl radical.

When $R_1$ is a saturated or unsaturated heterocyclic five-membered ring with 1 to 4 heteroatoms or a heterocyclic six-membered ring with 1 to 5 heteroatoms, the heteroatoms of the above-mentioned five- and six-membered rings being the same or different and being nitrogen, oxygen or sulphur and optionally carrying an oxygen atom on one or more nitrogen atoms, then, in this sense, there are preferred the pyrrole, furan, thiophene, pyrazole, imidazole, thiazole, isothiazole, oxazole, isoxazole, triazole, tetrazole, thiadiazole, oxadiazole, pyrazine, N,N'-dioxypyrazine, pyrimidine, N,N'-dioxypyrimidine, pyridazine, oxazine, thiazine, triazine, tetrazine, pyridine, N-oxypyridine, piperidine, piperazine, morpholine and thiomorpholine radicals.

Alkyl, alkoxy and alkylthio substituents in the heterocyclic five- and six-membered ring can contain up to 6 and preferably up to 4 carbon atoms, the methyl, ethyl, methoxy, ethoxy, methylthio and ethylthio radicals being preferred.

Halogen is to be understood to be fluorine, chlorine or bromine and preferably chlorine.

If the saturated or unsaturated heterocyclic five- and six-membered rings are condensed with a phenyl ring, then there are preferred the indole, indazole, benzimidazole, quinoline, isoquinoline, cinnoline, phthalazine, quinazoline, quinoxaline, benzofuran, benzothiophene, benzoxazole, benzisoxazole, benzothiazole and benzisothiazole radicals.

When X is a valency bond and $R_1$ is an alkyl, alkenyl or alkynyl radical, then these radicals are to be understood to be straight or branched chained with up to 10 carbon atoms.

Preferred in this sense for $R_1$ is the methyl, ethyl, propyl, butyl, pentyl, hexyl, vinyl, propenyl and propionyl radical. When X is a valency bond and $R_1$ is a cycloalkyl or cycloalkenyl radical, then these are to be understood to be rings with 3 to 7 members. Preferred in this sense are the cyclopropyl, cyclobutyl, cyclopentyl, cyclohexyl, cyclopentenyl and cyclohexenyl radical. When X is a valency bond and $R_1$ is a haloalkyl, alkoxyalkyl, carboxyalkyl, alkoxycarbonylalkyl, aminoalkyl, hydroxyalkyl, alkoxycarbonylaminoalkyl, alkylsulphonylaminoalkyl, alkylthio or an alkylcarbonylamino radical, then the alkyl or alkoxy moieties can contain up to 6 carbon atoms. Halogen is to be understood to be fluorine or chlorine and preferably fluorine.

Preferred in this sense for $R_1$ is the trifluoromethyl, ethoxymethyl, methoxyethyl, ethoxyethyl, carboxymethyl, carboxypropyl, carboxybutyl, methoxycarbonylmethyl, methoxycarbonylethyl, methoxycarbonylpropyl, ethoxycarbonylmethyl, ethoxycarbonylethyl, ethoxycarbonylpropyl, propoxycarbonylethyl, aminomethyl, aminoethyl, aminopropyl, aminobutyl, methylthio, ethylthio, propylthio, butylthio, acetylamino, propionylamino, butyloxycarbonylamino, methylsulphonylamino, formylaminopropyl, acetylaminopropyl, propionylaminopropyl and methylsulphonylaminopropyl radical.

When, in general formula I, X is an alkylene radical, then thereunder are to be understood alkylene radicals containing up to 4 carbon atoms, preferred in this sense being the methylene and ethylene radicals.

For A, B, C and D in general formula I, those compounds are preferred in which one or two of A, B, C and D are nitrogen atoms and the others are carbon atoms which can be substituted by hydrogen atoms, $C_1-C_6$-alkyl radicals or $C_3-C_7$-cycloalkyl radicals, whereby the carbon atoms can additionally also carry hydroxyl or oxo groups or can be part of a spirocycle containing 3 to 7 carbon atoms.

Preferred tricyclic ring systems of general formula I are 5,6,7,8-tetrahydro-1H-imidazo[4,5-g]-quinolin-6-one, 7,8-dihydro-1H-imidazo[4,5-g]quinazolin-8-one, 2,3,5,6,7,8-hexahydro-1H-imidazo[4,5-g]quinolin-2,6-dione, 5,6,7,8-tetrahydro-1H-imidazo[4,5-g]isoquinolin-5-one, 5,6-dihydro-1H-imidazo[4,5-g]isoquinolin-5-one, 5,6,7,8-tetrahydro-1H-imidazo[4,5-g]isoquinolin-5,7-dione, 5,6-dihydro-1H-imidazo[4,5-g]quinoxalin-6-one, 5,6,7,8-tetrahydro-1H-imidazo[4,5-g]quinoxalin-6,7-dione, 1H-imidazo[4,5-g]cinnoline, 5,6,7,8-tetrahydro-1H-imidazo[4,5-g]phthalazine-5,8-dione, 6,7-dihydro-1H,8H-imidazo[4,5-g]benzoxazin-7-one, 6,7-dihydro-1H,8H-imidazo[4,5-g]benzthiazin-7-one, 5,6,7,8-tetrahydro-1H-imidazo[4,5-g]quinolin-6-one and 5,6,7,8-tetrahydro-1H-imidazo[4,5-g]quinoline-one.

Especially preferred compounds of general formula I are those in which $R_1$ is a phenyl radical of general formula II, in which $R_2$ is a hydrogen atom, a methanesulphonyloxy, trifluoromethanesulphonyloxy, methanesulphonylamino, trifluoromethanesulphonylamino, methanesulphonylmethylamino, trifluoromethanesulphonylmethylamino, methylsulphenylmethyl, methylsulphinylmethyl, methylsulphonylmethyl, aminocarbonyl, aminosulphonyl, methylaminosulphonyl, dimethylaminosulphonyl, acetylamino, methylthio, methylsulphinyl, methylsulphonyl, hydroxyl, methyl, methoxy, propargyloxy, cyanomethoxy, methoxycarbonylmethoxy, cyano, chloro, nitro, amino, dimethylamino, trifluoromethyl or 1-imidazolyl radical, $R_3$ is a hydrogen or chlorine atom or a methyl, methoxy or dimethylamino radical and $R_4$ is a hydrogen atom or a methoxy radical or $R_1$ is a pyrrole, furan, thiophene, pyrazole, imidazole, isothiazole, thiazole, oxazole, triazole, tetrazole, thiadiazole, isoxazole, oxadiazole, pyridine, N-oxypyridine, pyrazine, N,N'-dioxypyrazine, pyrimidine, N,N'-dioxypyrimidine, pyridazine, oxazine, thiazine, triazine, tetrazine, piperidine, piperazine, morpholine or thiomorpholine radical, as well as the methyl-, ethyl-, methoxy-, ethoxy-, methylthio-, ethylthio and chlorine-substituted derivatives thereof, or a naphthalene, indole, indazole, quinoline or isoquinoline radical, or, when X is a valency bond, besides the mentioned groups, $R_1$ is also a hydrogen atom, a methyl, ethyl, propyl, butyl, pentyl, hexyl, propenyl, cyclopentenyl, cyclohexyl, trifluoromethyl, hydroxyl, mercapto, methylthio, amino, acetylamino or formylamino radical, X is a valency bond, a methylene or vinylene radical or an imino or amide group (—CONH—) and, of A, B, C and D, at least one or two are nitrogen atoms and the others are carbon atoms, which can be substituted by hydrogen atoms or methyl radicals, and the carbon atoms can additionally also carry hydroxyl or oxo groups or can be components of a spirocycle containing 5 carbon atoms.

The compounds of general formula I can be prepared by processes known from the literature (see G. W. H. Cheeseman, R. F. Cookson in The Chemistry of Heterocyclic Compounds, ed.: A. Weissberger, E. Taylor, Vol. 35, page 78-111/1979; and P. N. Preston, D. M. Smith, G. Tennant, ebenda, Vol. 40, Part 1, page 1-286/1981).

Especially advantageous are the following processes in which:

a) a compound of the general formula:

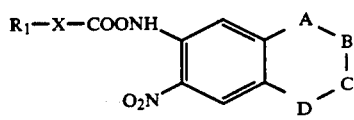
(III)

or of the general formula:

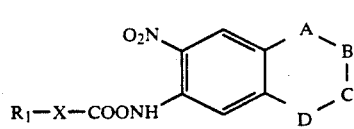
(IV)

in which $R_1$, X, A, B, C and D have the above-given meanings, is hydrogenated and cyclised to the benzimidazole; or b) a compound of the general formula V

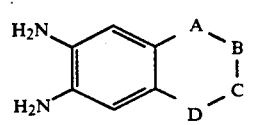
(V)

in which A, B, C and D have the above-given meanings, is reacted with a compound of the general formula:

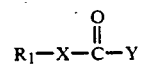
(VI)

in which $R_1$ and X have the above-given meanings and Y is a residue which is easily split off; or c) when $R_1$ in compounds of general formula I is an amino, hydroxyl or mercapto group and X is a valency bond, a compound of general formula V, in which A, B, C and D have the above-given meanings, is reacted with a reagent which transfers a carbonyl, thiocarbonyl or imino group, for example phosgene, thiophosgene, 1,1'-carbonyldiimidazole, a chloroformic acid ester, urea or cyanogen bromide; or d) when A and D in compounds of general formula I are nitrogen atoms, a compound of the general formula:

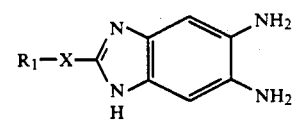
(VII)

in which $R_1$ and X have the above-given meanings, is cyclised with a compound of the general formula:

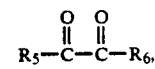
(VIII)

in which $R_5$ and $R_6$ are the same or different and are hydrogen or halogen atoms, alkyl or alkoxy radicals or hydroxyl groups to give compounds of general formula I, in which B and C are carbon atoms.

The reduction mentioned in process a is preferably carried out in a solvent or solvent mixture, such as water, methanol, ethanol, glacial acetic acid, ethyl acetate or dimethylformamide, with hydrogen in the presence of a catalyst, such as Raney nickel, platinum or palladium/charcoal, with a metal, such as iron, tin or zinc, in the presence of an acid, with a salt, such as ferrous sulphate, stannous chloride, sodium sulphide, sodium hydrogen sulphite or sodium dithionite, or with hydrazine in the presence of Raney nickel at a temperature of from 0° to 100° C. but preferably at ambient temperature. The cyclized compounds of general formula I are thereby mostly obtained directly.

If desired, the cyclisation can be completed by heating after the reduction, preferably in a solvent or solvent mixture, such as ethanol, isopropanol, glacial acetic acid, benzene, toluene, chlorobenzene, glycol, ethylene glycol dimethyl ether, sulfolan or dimethylformamide, to a temperature of from 50° to 220° C. but preferably to the boiling temperature of the reaction mixture, optionally in the presence of a condensation agent, such as phosphorus oxychloride, thionyl chloride, p-toluenesulphonic acid, hydrochloric acid, sulphuric acid, phosphoric acid or polyphosphoric acid, or optionally also in the presence of a base, such as sodium hydroxide, sodium methylate or potassium tert.-butylate. However, the cyclization can also be carried out without the use of a solvent and/or condensation agent.

The compounds of general formula VI used in process b are to be understood to be aldehydes, carboxylic acids, acid halides, such as acid chlorides, carboxylic acid esters, such as methyl and ethyl esters, carboxylic acid amides and other activated carboxylic acid derivatives, as well as anhydrides.

When the compound of general formula VI is an aldehyde, then the reaction with a compound of general formula V takes place under oxidising conditions, preferably in an alcoholic medium with heating under reflux in the presence of atmospheric oxygen and catalytic amounts of acid, such as toluenesulphonic acid, or in the presence of atmospheric oxygen and of a catalyst, such as pyrolusite, in an acidic medium, for example glacial acetic acid, at ambient temperature.

When the compound of general formula VI is a carboxylic acid, then the reaction with a compound of the general formula V takes place in the presence of a water-removing agent, preferably in polyphosphoric acid, at a temperature of from 50° to 250° C. and preferably of from 100° to 200° C.

When the compound of general formula VI is a carboxylic acid derivative, then the reaction with a compound of general formula V takes place in an inert solvent and preferably in methylene chloride or pyridine. For completion of the cyclization, heating is subsequently carried out in a solvent or solvent mixture, such as ethanol, isopropanol, glacial acetic acid, benzene, chlorobenzene, glycol, diethylene glycol dimethyl ether, sulfolan or dimethylformamide, to a temperature of from 50° to 250° C. but preferably to the boiling temperature of the solvent or solvent mixture, optionally in the presence of a condensation agent, such as phosphorus oxychloride, thionyl chloride, p-toluenesulphonic acid, hydrochloric acid, sulphuric acid, phosphoric acid or polyphosphoric acid, or optionally also in the presence of a base, such as sodium hydroxide, potassium methylate or potassium tert.-butylate. However, the cyclization can also be carried out without the use of a solvent and/or condensation agent.

The cyclization of compounds of general formula V described in process c to give compounds of general formula I is preferably carried out in that phosgene is passed into a hydrochloric acid solution of a compound of general formula V or thiophosgene is added thereto and left to stand at ambient temperature or a compound of general formula V is heated with cyanogen bromide or urea without a solvent or a compound of general formula V is heated to boil with 1,1'-carbonyldiimidazole in an inert solvent, such as dioxan.

The cyclization described in process d of the diamines VII with -dicarbonyl compounds VIII is preferably carried out without the use of a solvent or in a solvent or solvent mixture, such as water, methanol, ethanol, glacial acetic acid, ethyl acetate, dioxan, toluene or dimethylformamide, at a temperature of from 0° C. to the boiling point of the solvent and preferably at 50° to 100° C.

The compounds of general formula I obtained according to processes a–d and the tautomers thereof can, if desired, subsequently be converted into other compounds of general formula I and/or converted into physiologically acceptable salts with inorganic and organic acids.

The conversion of compounds of general formula I into other compounds of general formula I applies, for example, to the following:

a) For the reaction of a compound of general formula I, in which $R_1$ is an amino, aminoalkyl or cyclic imino group or is a heterocyclic five- or six-membered ring substituted with an amino group or is a phenyl radical of general formula II, in which one or more of the substituents $R_2$, $R_3$, $R_4$ is an amino group, with a carboxylic acid or activated carboxylic acid derivative, such as an anhydride or acid halide, to give a formylamino or alkylcarbonylamino derivative. Reactions with carboxylic acids are preferably carried out in the presence of a water-removing agent, such as polyphosphoric acid, or of a solvent forming an azeotropic mixture with water, such as benzene or toluene.

Reactions with activated carboxylic acid derivatives are preferably carried out in an inert solvent, such as methylene chloride or pyridine, at a temperature of from 0° C. to 250° C. but preferably at the boiling temperature of the solvent.

b) For the reaction of a compound of general formula I, in which $R_1$ is an amino, aminoalkyl or cyclic imino group or $R_1$ is a heterocyclic five- or six-membered ring substituted with an amino group, such as defined hereinbefore or $R_1$ is a phenyl radical of general formula II, in which one of the substituents $R_2$, $R_3$, $R_4$ is an amino, N-alkylamino or hydroxyl group, with a sulphonic acid of general formula:

$$R_7-SO_2OH \qquad (IX),$$

in which $R_7$ is an alkyl radical containing up to 3 carbon atoms or a trifluoromethyl radical, or with a reactive derivative hereof, to give a compound of general formula I in which the said amino, aminoalkyl, cyclic imino, N-alkylamino or hydroxyl groups are sulphonated.

The reaction is preferably carried out in a solvent or solvent mixture, such as methylene chloride, diethyl ether, tetrahydrofuran, dioxan or benzene, optionally in the presence of an acid-binding agent, such as sodium carbonate, triethylamine or pyridine, in which case the latter two can simultaneously be used as solvent, in the presence of an agent activating the acid or removing water, such as thionyl chloride or phosphorus pentachloride, but preferably with a reactive derivative of a compound of general formula IX, for example with an anhydride or halide thereof, such as methanesulphonic acid chloride or ethanesulphonic acid chloride, preferably at a temperature of from 0° to 100° C., for example at a temperature of from ambient temperature to 50° C.

c) For the conversion of a compound of general formula I, in which $R_1$ is a phenyl radical of general formula II, in which one of the substituents $R_2$, $R_3$, $R_4$ is an alkylthio or alkylsulphenylmethyl radical containing up to 3 carbon atoms in the alkyl moiety, to give a compound of general formula I, in which $R_1$ is a phenyl radical and one of the substituents $R_2$, $R_3$, $R_4$ is an alkylsulphinyl, alkylsulphonyl, alkylsulphinylmethyl or alkylsulphonylmethyl radical.

This oxidation is preferably carried out in a solvent or solvent mixture, for example in water, water/pyridine, acetone, glacial acetic acid, dilute sulphuric acid or trifluoroacetic acid, depending upon the oxidation agent used, preferably at a temperature of from $-80°$ to $100°$ C.

For the preparation of an alkylsulphinyl or alkylsulphinylmethyl compound of general formula I, the oxidation is preferably carried out with one equivalent of the oxidation agent used, for example with hydrogen peroxide in glacial acetic acid, trifluoroacetic acid or formic acid at $0°$ to $20°$ C. or in acetone at $0°$ to $60°$ C., with a per acid, such as performic acid, in glacial acetic acid or trifluoroacetic acid at $0°$ to $50°$ C. or with m-chloroperbenzoic acid in methylene chloride or chloroform at $-20°$ C. to $60°$ C., with sodium metaperiodate in aqueous methanol or ethanol at $-15°$ to $25°$ C., with bromine in glacial acetic acid or aqueous acetic acid, with N-bromosuccinimide in ethanol, with tert.-butyl hypochlorite in methanol at $-80°$ C. to $-30°$ C., with iodobenzodichloride in aqueous pyridine at $0°$ to $50°$ C., with nitric acid in glacial acetic acid at $0°$ to $20°$ C., with chromic acid in glacial acetic acid or in acetone at $0°$ to $20°$ C. and with sulphonyl chloride in methylene chloride at $-70°$ C., the thioether-chlorine complex hereby obtained preferably being hydrolysed with aqueous ethanol.

For the preparation of an alkylsulphonyl or alkylsulphonylmethyl compound of general formula I, the oxidation is preferably carried out with one or with two or more equivalents, respectively, of the oxidation agent used, for example hydrogen peroxide in glacial acetic acid, trifluoroacetic acid or formic acid at $20°$ to $100°$ C. or in acetone at $0°$ to $60°$ C., with a per acid, such as performic acid or m-chloroperbenzoic acid, in glacial acetic acid, trifluoroacetic acid, methylene chloride or chloroform at a temperature of from $0°$ to $60°$ C., with nitric acid in glacial acetic acid at $0°$ to $20°$ C., with chromic acid or potassium permanganate in glacial acetic acid, water/sulphuric acid or in acetone at $0°$ to $20°$ C.

d) For the conversion of a compound of general formula I, in which $R_1$ is a phenyl radical of general formula II, in which one of the substituents $R_2$, $R_3$, $R_4$ is a carboxyl or hydroxysulphonyl group, to give a compound of general formula I, in which one of the substituents $R_2$, $R_3$ and $R_4$ is a carbonyl or sulphonyl group substituted by an amino, alkylamino or dialkylamino group. This takes place by reaction with an amine $HNR_8R_9$, wherein $R_8$ and $R_9$ can be the same or different and are hydrogen atoms or $C_1$-$C_5$-alkyl radicals, or with a reactive derivative hereof. It is advantageous to convert the carboxyl group or hydroxysulphonyl group into a reactive derivative, for example into an ester of an acid chloride, and then to react with the amine $HNR_8R_9$.

The reaction is preferably carried out in a solvent or solvent mixture, such as methylene chloride, ethanol, chloroform, carbon tetrachloride, diethyl ether, tetrahydrofuran, dioxan, benzene, toluene, acetonitrile or dimethylformamide, optionally in the presence of an agent activating the acid or of a water-removing agent, for example in the presence of ethyl chloroformate, thionyl chloride, phosphorus trichloride, phosphorus pentoxide, N′,N-dicyclohexylcarbodiimide/N-hydroxysuccinimide, N,N′-carbonyldiimidazole or N,N′-thionyldiimidazole or triphenylphosphine/carbon tetrachloride, or of an agent activating the amino group, for example phosphorus trichloride, and optionally in the presence of an inorganic base, such as sodium carbonate, or of a tertiary organic base, such as triethylamine or pyridine, which can simultaneously serve as solvent, at a temperature of from $-25°$ to $250°$ C. but preferably at a temperature of from $-10°$ C. to the boiling temperature of the solvent used. Furthermore, water formed during the reaction can be removed by azeotropic distillation, for example by heating with toluene on a water separator, or by the addition of a drying agent, such as anhydrous magnesium sulphate or a molecular sieve.

However, the reaction is especially advantageously carried out in a corresponding halide, for example the carboxylic acid or sulphonic acid chloride, and an appropriate amine, whereby this can simultaneously serve as a solvent, and at a temperature of from $0°$ to $50°$ C.

e) For the conversion of a compound of general formula I, in which $R_1$ is a phenyl radical of general formula II and one of the substituents $R_2$, $R_3$ or $R_4$ is a cyano group, to give a compound of general formula I, in which $R_1$ is a phenyl radical of general formula II and one of the substituents $R_2$, $R_3$ or $R_4$ is an alkoxycarbonyl radical or an aminocarbonyl or carboxyl group.

This alcoholysis and/or hydrolysis is carried out either in the presence of an acid, such as hydrochloric acid, sulphuric acid, phosphoric acid or trichloroacetic acid, or in the presence of a base, such as sodium hydroxide or potassium hydroxide, in an appropriate solvent, such as water, water/methanol, ethanol, water/ethanol, water/isopropanol or water/dioxan, at a temperature of from $-10°$ to $120°$ C., for example at a temperature of from ambient temperature to the boiling temperature of the reaction mixture.

f) For the alkylation of a compound of general formula I, in which $R_1$ is a phenyl radical of general formula II, in which one of the substituents $R_2$, $R_3$ or $R_4$ is a hydroxyl or mercapto group, or in which $R_1$ is a heterocyclic ring substituted with a hydroxyl or mercapto group or in which X is a valency bond and $R_1$ is a hydroxyl or mercapto group, the corresponding alkylthio or alkoxy compounds thereby being obtained.

The reaction is preferably carried out in a solvent, such as acetone, diethyl ether, benzene, toluene or dimethylformamide, at a temperature of from $-30°$ C. to $100°$ C. and preferably at ambient temperature, in the presence of a base, such as potassium carbonate or sodium hydride, and of an alkylation agent, such as an alkyl halide or alkyl sulphate.

g) For the reduction of a compound of general formula I, in which $R_1$ is a pyridine ring, to give a compound of general formula I, in which $R_1$ is a piperidine ring. This reduction is preferably carried out in an alcoholic medium in the presence of a catalyst, such as platinum or palladium, by means of hydrogen at normal pressure or at a slightly elevated pressure and at a temperature of from ambient temperature to $60°$ C.

h) For the hydrogenation of a vinyl compound $(X=-CH=CH-)$ to give the corresponding ethyl compound $(X=-CH_2-CH_2-)$. The hydrogenation is preferably carried out in a solvent, such as water, water/ethanol, methanol, glacial acetic acid, ethyl acetate or dimethylformamide, preferably with hydrogen in the presence of a hydrogenation catalyst, such as Raney nickel, platinum or palladium/charcoal.

i) For the oxidation of a five- or six-membered ring with one or more nitrogen atoms to the corresponding N-oxide. The oxidation is preferably carried out with one or more equivalents of the oxidation agent used, for example with hydrogen peroxide in glacial acetic acid, trifluoroacetic acid or formic acid at 20° to 100° C. or in acetone at 0° to 60° C., with a per acid, such as performic acid or m-chloroperbenzoic acid, in glacial acetic acid, trifluoroacetic acid, methylene chloride or chloroform, at a temperature of from 0° to 60° C.

j) For the conversion of a compound of the general formula:

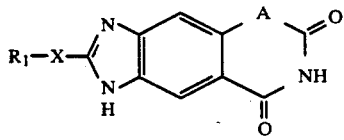
(Ia)

in which $R_1$ and X have the above-given meanings and A is a carbon atom with two alkyl radicals, to give a compound of the general formula:

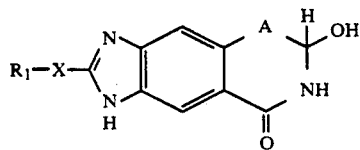
(Ib)

in which $R_1$ and X have the above-given meanings and A is a carbon atom with two alkyl radicals.

The conversion is advantageously carried out in a solvent or solvent mixture, such as methanol, ethanol, dioxan, tetrahydrofuran, water or dimethylformamide, in the presence of a reducing agent, such as sodium borohydride, sodium cyanoborohydride, lithium aluminium hydride or some other complex hydride or with borane or by catalytic hydrogenation, at a temperature of from −20° C. to 100° C.

k) For the conversion of a compound of general formula Ib into a compound of general formula:

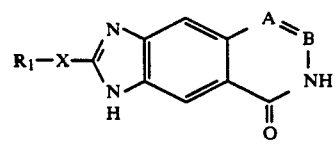
(Ic)

in which $R_1$ and X have the above-given meanings and A and B are carbon atoms which are substituted by an alkyl radical.

This conversion is carried out in a solvent or solvent mixture, such as methanol, ethanol, dioxan, tetrahydrofuran, chloroform or dimethylformamide, in the presence of an acid, which itself can also serve as solvent, such as sulphuric acid, hydrochloric acid, nitric acid, polyphosphoric acid or hydrofluoric acid, or with a Lewis acid, such as aluminium chloride, stannic chloride, zinc chloride, boron trifluoride or titanium tetrachloride, at a temperature of from -20° C. to 50° C.

l) For the reaction of a compound of the general formula:

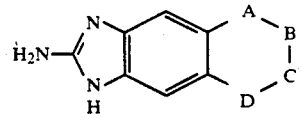
(Id)

in which A, 8, C and D have the above-given meanings, with a compound of the general formula:

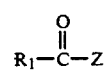
(X)

in which $R_1$ has the above-given meaning and Z, together with the C=O group, represents a carboxylic acid, carboxylic acid halide, ester or some other activated carboxylic acid derivative or anhydride, to give a compound of general formula I, in which $R_1$, A, B, C and D have the above-mentioned meanings and X is an amide group (—CONH—).

The reaction is carried out in a solvent or solvent mixture, such as ethanol, isopropanol, glacial acetic acid, benzene, chlorobenzene, glycol, diethylene glycol dimethyl ether, methylene chloride, pyridine, sulfolan or dimethylformamide, optionally with the addition of an adjuvant base, such as triethylamine, sodium carbonate or sodium hydroxide, or of a condensation agent, such as phosphorus oxychloride, thionyl chloride or polyphosphoric acid, at a temperature of from −20° C. to 250° C. and preferably of from 0° C. to the boiling point of the solvent.

Furthermore, the compounds obtained of general formula I can subsequently, if desired, be converted into their physiologically acceptable acid addition salts with inorganic and organic acids. As acids herefor there can be used, for example, hydrochloric acid, hydrobromic acid, sulphuric acid, phosphoric acid, fumaric acid, succinic acid, tartaric acid, citric acid, lactic acid, maleic acid or methanesulphonic acid.

As already mentioned hereinbefore, the new compounds of general formula I, their tautomers, optically-active compounds and racemates and their physiologically acceptable acid addition salts display superior pharmacological properties. In particular, they inhibit the aggregation of thrombocytes and erythrocytes and/or lower the blood pressure and/or increase the heart power.

For the preparation of pharmaceutical compositions, the compounds of general formula I are mixed in known manner with appropriate pharmaceutical carrier substances, aroma, flavouring and colouring materials and formed, for example, into tablets or dragees or, with the addition of appropriate adjuvants, suspended or dissolved in water or an oil, such as olive oil.

The new compounds of general formula I according to the present invention and the salts thereof can be administered enterally or parenterally in liquid or solid form. As injection medium, there is preferably used water which contains the additives usual in the case of injection solutions, such as stabilising agents, solubilising agents and/or buffers.

Such additives include, for example, tartrate and citrate buffers, ethanol, complex formers (such as ethylenediamine-tetraacetic acid and non-toxic salts thereof) and high molecular weight polymers (such as liquid polyethylene oxide) for viscosity regulation. Solid carrier materials include, for example, starch, lactose, mannitol, methyl cellulose, talc, highly dispersed silicic acids, high molecular weight fatty acids (such as stearic acid), gelatine, agar-agar, calcium phosphate, magnesium stearate, animal and vegetable fats and solid high molecular weight polymers (such as polyethylene glycol). Compositions suitable for oral administration can, if desired, contain flavouring and sweetening materials.

The compounds according to the present invention are usually administered in amounts of from 1 to 500 mg. per day, referred to 75 kg. body weight. It is preferred to administer 2 to 3 times per day 1 to 2 tablets with an active material content of 1 to 200 mg. The tablets can also be retarded, in which case 1 or 2 tablets with 1 to 500 mg. of active material have to be given once per day. The active material can also be given by injection 1 to 8 times per day or by continuous infusion, amounts of from 0.1 to 200 mg./day thereby normally sufficing.

Especially preferred according to the present invention are, apart from the compounds mentioned in the Examples, the following and the tautomers thereof:

7,7-dimethyl-2-(4-methoxyphenyl)-5,6,7,8-tetrahydro-1H-imidazo[4,5-g]quinolin-6-one
7,7-dimethyl-2-(4-methylphenyl)-5,6,7,8-tetrahydro-1H-imidazo[4,5-g]quinolin-6-one
7,7-dimethyl-2-(4-trifluoromethylphenyl)-5,6,7,8-tetrahydro-1H-imidazo[4,5-g]quinolin-6-one
7,7-dimethyl-2-(2-methoxy-4-methylphenyl)-5,6,7,8-tetrahydro-1H-imidazo[4,5-g]quinolin-6-one
7,7-dimethyl-2-(2-methoxy-4-methylthiophenyl)-5,6,7,8-tetrahydro-1H-imidazo[4,5-g]quinolin-6-one
7,7-dimethyl-2-(2-methoxy-4-methylsulphinylphenyl)-5,6,7,8-tetrahydro-1H-imidazo[4,5-g]quinolin-6-one
2'-(4-methoxyphenyl)-spiro[cyclopentan-1,7'-5',6',7',8'-tetrahydro-1'H-imidazo[4',5'-g]quinolin]-6'-one
2'-(2-methoxy-4-methylsulphinylphenyl)-spiro[cyclopentan-1,7'-5',6',7',8'-tetrahydro-'H-imidazo[4',5'-g]quinolin]-6'-one
2-(2-methoxy-4-methylsulphinylphenyl)-7,8-dihydro-1H-imidazo[4,5-g]quinazolin-8-one
2-(2-methoxy-4-methylsulphonylphenyl)-7,8-dihydro-1H-imidazo[4,5-g]quinazolin-8-one
8,8-dimethyl-2,3,5,6,7,8-hexahydro-1H-imidazo[4,5-g]quinoline-2,6-dione
8,8-dimethyl-2-amino-5,6,7,8-tetrahydro-1H-imidazo-4,5-g]quinolin-6-one
8,8-dimethyl-2-(prop-1-en-1-yl)-5,6,7,8-tetrahydro-1H-imidazo[4,5-g]quinolin-6-one
8,8-dimethyl-2-(pent-1-en-1-yl)-5,6,7,8-tetrahydro-1H-imidazo[4,5-g]quinolin-6-one
8,8-dimethyl-2-(pent-1,3-dien-1-yl)-5,6,7,8-tetrahydro-1H-imidazo[4,5-g]quinolin-6-one
8,8-dimethyl-2-(2-ethoxycarbonylmethyloxyphenyl)-5,6,7,8-tetrahydro-1H-imidazo[4,5-g]quinolin-6-one
8,8-dimethyl-2-(2-methylthiophenyl)-5,6,7,8-tetrahydro-1H-imidazo[4,5-g]quinolin-6-one
8,8-dimethyl-2-(4-acetylaminophenyl)-5,6,7,8-tetrahydro-1H-imidazo[4,5-g]quinolin-6-one
8,8-dimethyl-2-(4-aminosulphonylphenyl)-5,6,7,8-tetrahydro-1H-imidazo[4,5-g]quinolin-6-one
8,8-dimethyl-2-(4-morpholinosulphonylphenyl)-5,6,7,8-tetrahydro-1H-imidazo[4,5-g]quinolin-6-one
8,8-dimethyl-2-(2-methoxy-4-methylsulphonylphenyl)-5,6,7,8-tetrahydro-1H-imidazo[4,5-g]quinolin-6-one
8,8-dimethyl-2-(2-pyrrolyl)-5,6,7,8-tetrahydro-1H-imidazo[4,5-g]quinolin-6-one
8,8-dimethyl-2-(1-imidazolyl)-5,6,7,8-tetrahydro-1H-imidazo[4,5-g]quinolin-6-one
8,8-dimethyl-2-(2-methyl-4-oxazolyl)-5,6,7,8-tetrahydro-1H-imidazo[4,5-g]quinolin-6-one
8,8-dimethyl-2-(5-isoxazolyl)-5,6,7,8-tetrahydro-1H-imidazo[4,5-g]quinolin-6-one
8,8-dimethyl-2-(4-thiazolyl)-5,6,7,8-tetrahydro-1H-imidazo[4,5-g]quinolin-6-one
8,8-dimethyl-2-(1,2,4-triazol-5-yl)-5,6,7,8-tetrahydro-1H-imidazo[4,5-g]quinolin-6-one
8,8-dimethyl-2-(1,2,5-thiadiazol-3-yl)-5,6,7,8-tetrahydro-1H-imidazo[4,5-g]quinolin-6-one
8,8-dimethyl-2-(1,2,3-thiadiazol-4-yl)-5,6,7,8-tetrahydro-1H-imidazo[4,5-g]quinolin-6-one
8,8-dimethyl-2-(1,2,3-thiadiazol-5-yl)-5,6,7,8-tetrahydro-1H-imidazo[4,5-g]quinolin-6-one
8,8-dimethyl-2-(2-methylthio-1,3,4-oxadiazol-5-yl)-5,6,7,8-tetrahydro-1H-imidazo[4,5-g]quinolin-6-one
8,8-dimethyl-2-(2-pyridyl)-5,6,7,8-tetrahydro-1H-imidazo[4,5-g]quinolin-6-one
8,8-dimethyl-2-(4-thiomorpholinyl)-5,6,7,8-tetrahydro-1H-imidazo[4,5-g]quinolin-6-one
8,8-dimethyl-2-(2-naphthyl)-5,6,7,8-tetrahydro-1H-imidazo[4,5-g]quinolin-6-one
8,8-dimethyl-2-(2-benzofuranyl)-5,6,7,8-tetrahydro-1H-imidazo[4,5-g]quinolin-6-one
8,8-dimethyl-2-(3-quinolinyl)-5,6,7,8-tetrahydro-1H-imidazo[4,5-g]quinolin-6-one
2'-(4-methoxyphenyl)-spiro[cyclopentane-1,8'-5',6',7',8'-tetrahydro-1H-imidazo[4',5'-g]quinolin]-6'-one
2'-(4-methylphenyl)-spiro[cyclopentane-1,8'-5',6',7',8'-tetrahydro-1'H-imidazo[4',5'-g]quinolin]-6'-one
2'-(4-trifluoromethylphenyl)-spiro[cyclopentane-1,8'-5',6',7',8'-tetrahydro-1'H-imidazo[4'5'-g]quinolin]-6'-one
2'-(2-methoxy-4-methylthiophenyl)-spiro[cyclopentane-1,8'-5',6',7',8'-tetrahydro-1'H-imidazo[4',5'-g]quinolin]-6'-one
2'-(2-methoxy-4-methylsulphonylphenyl)-spiro[cyclopentane-1,8'-5',6',7',8'-tetrahydro-1'H-imidazo-[4',5'-g]quinolin]-6'-one
2'-(2-methoxy-4-methylsulphonyloxyphenyl)-spiro[cyclopentane-1,8'-5',6',7',8'-tetrahydro-1'H-imidazo-4',5'-g]quinolin]-6'-one
2'-(quinolin-4-yl)-spiro[cyclopentane-1,8'-5',6',7',8'-tetrahydro-1'H-imidazo[4',5'-g]quinolin]-6'-one
2'-(3-methylpyrazol-5-yl)-spiro[cyclopentane-1,8'-5',6',7',8'-tetrahydro-1'H-imidazo[4',5'-g]quinolin]-6'-one
2'-(4-methoxyphenyl)-spiro[cyclohexane-1,8'-5',6',7',8'-tetrahydro-1'H-imidazo[4',5'-g]quinolin]-6'-one
8,8-dimethyl-2-(4-methoxyphenyl)-5,6,7,8-tetrahydro-1H-imidazo[4,5-g]isoquinolin-5-one
8,8-dimethyl-2-(4-trifluoromethylphenyl)-5,6,7,8-tetrahydro-1H-imidazo[4,5-g]isoquinolin-5-one
8,8-dimethyl-2-(2-methoxy-4-methylphenyl)-5,6,7,8-tetrahydro-1H-imidazo[4,5-g]isoquinolin-5-one
8,8-dimethyl-2-(2-methoxy-4-methylthiophenyl)-5,6,7,8-tetrahydro-1H-imidazo[4,5-g]isoquinolin-5-one
8,8-dimethyl-2-(2-methoxy-4-methylsulphinylphenyl)-5,6,7,8-tetrahydro-1H-imidazo[4,5-g]isoquinolin-5-one
8,8-dimethyl-2-(2-methoxy-4-methylsulphonyloxyphenyl)-5,6,7,8-tetrahydro-1H-imidazo[4,5-g]isoquinolin-5-one 8,8-dimethyl-2-(2-methoxy-4-methylsulphonylphenyl)-5,6,7,8-tetrahydro-1H-imidazo[4,5-g]isoquinolin-5-one 8,8-dimethyl-2-(quinolin-4-yl)-5,6,7,8-tetrahydro-1H-imidazo[4,5-g]isoquinolin-5-one 8,8-dimethyl-2-(3-methylpyrazol-5-yl)-5,6,7,8-tetrahydro-1H-imidazo[4,5-g]isoquinolin-5-one 2'-(4-methoxyphenyl)-spiro[cyclopentane-1,8'-5',6',7',8'-tetrahydro-1'H-imidazo[4',5'-g]isoquinolin]-5'-one 2'-(4-methylphenyl)-spiro[cyclopentane-1,8'-5',6',7',8'-tetrahydro-1'H-imidazo[4',5'-g]isoquinolin]-5'-one 2'-(4-trifluoromethylphenyl)-spiro[cyclopentane-1,8',-5',6',7',8'-tetrahydro-1'H-imidazo[4',5'-g]isoquinolin]-5'-one 2'-(2-methoxy-4-methylthiophenyl)-spiro[cyclopentane-1,8'-5',6',7',8'-tetrahydro-1'H-imidazo[4',5'-g]isoquinolin]-5'-one 2'-(2-methoxy-4-methylsulphinylphenyl)-spiro[cyclopentane-1,8'-5',6',7',8'-tetrahydro-1'H-imidazo[4',5'-g]-isoquinolin]-5'-one 2'-(2-methoxy-4-methylsulphonylphenyl)-spiro[cyclopentane-1,8'-5',6',7',8'-tetrahydro-1'H-imidazo[4',5'-g]isoquinolin]-5'-one 2'-(2-methoxy-4-methylsulphonyloxyphenyl)-spiro[cyclopentane-1,8'-5',6',7',8'-tetrahydro-1'H-imidazo-4',5'-g]isoquinolin]-5'-one 2'-(quinolin-4-yl)-spiro[cyclopentane-1,8'-5',6',7',8'-tetrahydro-1'H-imidazo[4',5'-g]isoquinolin]-5'-one 2'-(3-methylpyrazol-5-yl)-spiro[cyclopentane-1,8',-6',7',8'-tetrahydro-1'H-imidazo[4',5'-g]isoquinolin]-5'-one 7,8-dimethyl-2-(4-methoxyphenyl)-5,6-dihydro-1H-imidazo[4,5-g]isoquinolin-5-one 7,8-dimethyl-2-(2-methoxy-4-methylthiophenyl)-5,6-dihydro-1H-imidazo[4,5-g]isoquinolin-5-one 7,8-dimethyl-2-(2-methoxy-4-methylsulphinylphenyl)-5,6-dihydro-1H-imidazo[4,5-g]isoquinolin-5-one 7, 8-dimethyl-2-(2-methoxy-4-methylsulphonylphenyl)-5,6-dihydro-1H-imidazo[4,5-g]isoquinolin-5-one 7,8-dimethyl-2-(2-methoxy-4-methylsulphonyloxyphenyl)-5,6-dihydro-1H-imidazo[4,5-g]isoquinolin-5-one 8,8-dimethyl-2-(4-methoxyphenyl)-5,6,7,8-tetrahydro-1H-imidazo[4,5-g]isoquinoline-5,7-dione 8,8-dimethyl-2-(2-methoxy-4-methylsulphinylphenyl)-5,6,7,8-tetrahydro-1H-imidazo[4,5-g]isoquinoline-5,7dione 8,8-dimethyl-2-(2-methoxy-4-methylsulphonylphenyl)-5,6,7,8-tetrahydro-1H-imidazo[4,5-g]isoquinoline-5,7dione 2'-(4-methoxyphenyl)-spiro[cyclopentane-1,8',-5',6',7',8'-tetrahydro-1'H-imidazo[4',5'-g]isoquinoline]-5',7'-dione 2'-(2-methoxy-4-methylsulphinylphenyl)-spiro[cyclopentane-1,8'-5',6',7',8'-tetrahydro-1'H-imidazo-4',5'-g]isoquinoline]-5',7'-dione 2'-(Z-methoxy-4-methylsulphonylphenyl)-spirocyclopentane-1,8'-5',6',7',8'-tetrahydro-1'H-imidazo-4',5'-isoquinoline]-5',7'-dione 2-(4-methoxyphenyl)-5,6-dihydro-1H-imidazo[4,5-g]-quinoxalin-6-one 2-(2-methoxy-4-methylsulphinylphenyl)-5,6-dihydro-1H-imidazo[4,5-g]quinoxalin-6-one 2-(2-methoxy-4-methylsulphonylphenyl)-5,6-dihydro-1H-imidazo[4,5-g]quinoxalin-6-one 2-(4-methoxyphenyl)-5,6,7,8-tetrahydro-1H-imidazo-[4,5-g]quinoxaline-6,7-dione 2-(2-methoxy-4-methylsulphinylphenyl)-5,6,7,8-tetrahydro-1H-imidazo[4,5-g]quinoxaline-6,7-dione 2-(2-methoxy-4-methylsulphonylphenyl)-5,6,7,8-tetrahydro-1H-imidazo[4,5-g]quinoxaline-6,7-dione 5,8-dimethyl-2-(4-methoxyphenyl)-5,6,7,8-tetrahydro-1H-imidazo[4,5-g]quinoxaline-6,7-dione 5,8-dimethyl-2-(2-methoxy-4-methylsulphinylphenyl)-5,6,7,8-tetrahydro-1H-imidazo[4,5-g]quinoxaline-6,7dion 5,8-dimethyl-2-(2-methoxy-4-methylsulphonylphenyl)-5,6,7,8-tetrahydro-1H-imidazo[4,5-g]quinoxaline-6,7dione 2-(4-pyridyl)-1H-imidazo[4,5-g]cinnoline 2-(4-methoxyphenyl)-1H-imidazo[4,5-g]cinnoline 2-(2-methoxy-4-methylsulphinylphenyl)-1H-imidazo[4,5-g]-cinnoline 2-(4-pyridyl)-5,6,7,8-tetrahydro-1H-imidazo[4,5-g]-phthalazine-5,8-dione 2-(4-methoxyphenyl)-5,6,7,8-tetrahydro-1H-imidazo-4,5-g]-phthalazine-5,8-dione 2-(4-pyridyl)-6,7-dihydro-1H,8H-imidazo[4,5-g]benzoxazin-7-one 2-(4-methoxyphenyl)-6,7-dihydro-1H,8H-imidazo[4,5-g]-benzoxazin-7-one 2-(4-pyridyl)-6,7-dihydro-1H,8H-imidazo[4,5-g]benzthiazin-7-one 2-(4-methoxyphenyl)-6,7-dihydro-1H,8H-imidazo[4,5-g]-benzthiazin-7-one The following Examples are given for the purpose of illustrating the present invention:

EXAMPLE 1

7,7-Dimethyl-2-(4-pyridyl)-5,6,7,8-tetrahydro-1H-imidazo[4,5-g]quinolin-6-one×0.5 mole isopropanol 3 g. (8.8 mmole) 3,3-Dimethyl-6-nitro-7-isonicotinoylamino-1,2,3,4-tetrahydroquinolin-2-one were suspended in 300 ml. ethanol, 0.3 g. 10% palladium/charcoal was added thereto and the mixture hydrogenated. After filtering off the catalyst, the filtrate was evaporated and stirred for one hour with glacial acetic acid at 60° C. After evaporation, neutralization and recrystallization from isopropanol, there was obtained 1.9 g. (74%,of theory) of the title compound; m.p. >300° C.

The starting material was prepared as follows:

a) 24.55 g. (137 mmole) 2,2-dimethyl-3-phenylpropionic acid were first mixed, while cooling with ice, with 180 ml. 96% nitric acid and subsequently maintained for 1 hour at 100° C. Working up (ice, methylene chloride, anhydrous magnesium sulphate) and recrystallisation from toluene/CH₂Cl₂ gave 19.8 g. (54% of theory) 2,2-dimethyl-3-(2,4-dinitrophenyl)-propionic acid; m.p. 120°-122° C.

b) 21.8 g. (81 mmole) of the above acid were esterified in ethanol in the presence of a catalytic amount of concentrated sulphuric acid. After working up (diethyl ether, aqueous sodium bicarbonate solution, anhydrous magnesium sulphate), there were obtained 23.8 g. of the ester in the form of an oil.

c) 23.8 g. (80 mmole) of the above ester were hydrogenated in ethanol in the presence of 10% palladium/charcoal. After separating off the catalyst and evaporating the ethanol, there were obtained 12.9 g. (85%) 7-amino-3,3-dimethyl-1,2,3,4-tetrahydroquinolin-2-one; m.p. 232°-235° C.

d) 12.5 g. (65 mmole) of the above amine were acylated with 12.9 g. (72 mmole) isonicotinic acid chloride hydrochloride in 400 ml. methylene chloride and 19.9 ml. triethylamine. Working up of the evaporation residue took place by treatment with water and recrystallization, with the addition of charcoal, from isopropanol to give 15.4 g. (79%) 7-isonicotinoylamino-3,3-dimethyl-1,2,3,4-tetrahydroquinolin-2-one; m.p. 242°-244° C.

e) 15.4 g. (52 mmole) of the above amide were nitrated at −30° C. in 300 ml. 96% nitric acid. After working up (ice, neutralisation, suction filtration), the residue was purified over silica gel (elution agent: methylene chloride/1% methanol) to give 6 g. (33%) 6-nitro-7-isonicotinoylamino-3,3-dimethyl-1,2,3,4-tetrahydroquinolin-2-one; m.p. 145°-148° C.

EXAMPLE 2

2-(4-Pyridyl)-7,8-dihydro-1H-imidazo[4,5-g]-quinazolin-8-one×H2O×HCl 2.9 g. (1.64 mmole) 6,7-diamino-3,4-dihydroquinazolin-4-one (J. Org. Chem. 40, 360/1975) were acylated in 145 ml. dimethylformamide with 4.35 g. (2.44 mmole) isonicotinic acid chloride hydrochloride and 7.4 g. triethylamine. After 4 hours, the reaction mixture was evaporated, the residue was mixed with water, suction filtered and the residue stirred with 250 ml. hot ethanol and filtered off with suction. The crystals obtained were subsequently heated under reflux for 24 hours with 75 ml. ethanol and 120 ml. concentrated hydrochloric acid, filtered off with suction, dissolved in 2N aqueous sodium hydroxide solution, charcoaled, acidified with concentrated hydrochloric acid and filtered off with suction to give 1.8 g. of the title compound in the form of its hydrochloride; m.p. >300° C.

EXAMPLE 2a 2-(4-Methoxyphenyl)-7,8-dihydro-1H-imidazo[4,5-g]-quinazolin-8-one.

In a manner analogous to that described in Example 20, from 4-methoxy-benzaldehyde, sodium hydrogen sulphite and 6,7-diamino-3,4-dihydroquinazolin-4-one (see Example 2), after boiling with methanol, there was obtained the title compound in a yield of 82% of theory; m.p. >300° C.

EXAMPLE 3

2-(4-Pyridyl)-5,6-dihydro-1H-imidazo[4,5-g]-quinoxalin-6-one.

3 g. (11.8 mmole) 2-(4-pyridyl)-5-amino-6-nitrobenzimidazole were hydrogenated in 500 ml. methanol in the presence of 0.8 g. platinum oxide. After filtering off the catalyst, the filtrate was mixed with 10 ml. glyoxylic acid ethyl ester and boiled for 3 hours under nitrogen at 60° C. After evaporation of the methanol, the residue was filtered off with suction while warm and the crystals obtained again recrystallized from methanol with the addition of charcoal to give 1.5 g. (48.5% of theory) of the title compound; m.p. >320° C.

The starting material was prepared as follows: 4.6 g. (27.4 mmole) 1,2,4-triamine-5-nitrobenzene (Org. Synth. 40, 96) were suspended in 60 ml. methylene chloride and acylated with 6.55 g. isonicotinic acid chloride hydrochloride and 11.4 ml. triethylamine. Subsequently, the methylene chloride was evaporated off, the residue was worked up with water and the still moist residue was refluxed with 250 ml. ethanol and 40 ml. concentrated hydrochloric acid for 20 hours. The evaporation residue was substantially dissolved in 250 ml. water, neutralized, filtered off with suction, boiled up with ethanol, evaporated and the crystals filtered off with suction to give 5.5 g. (79% of theory) 2-(4-pyridyl)-5-amino-6-nitrobenzimidazole.

EXAMPLE 4

8,8-Dimethyl-2-(4-methoxyphenyl)-5,6,7,8-tetrahydro-1H-imidazo[4,5-g]quinolin-6-one 6.8 g. (18.4 mmole) 4,4-dimethyl-6-(4-methoxybenzoylamino)-7-nitro-1,2,3,4-tetrahydroquinolin-2-one were hydrogenated in 200 ml. ethanol in the presence of 0.6 g. 10% palladium on charcoal. After filtering off of the catalyst, the filtrate was mixed with 15 ml. concentrated hydrochloric acid and boiled under reflux for 20 hours. The evaporation residue was mixed with water and ammonia, extracted with methylene chloride/methanol (20:1 v/v), purified over silica gel (elution agent: methylene chloride/ammonia-saturated methanol; 20:1 v/v) and recrystallized from ethanol to give 3.5 g. (60% of theory) of the title compound; m.p. 235°-238° C.

The starting material was prepared as follows: a) 29 g. (165 mmole) 3,3-dimethylacrylic acid anilide were thoroughly mixed with 58 g. aluminium chloride and 70 g. sodium chloride and, after subsidence of the exothermal reaction, heated to 100° C. for 2 hours. After . decomposing with ice, extracting, drying and evaporation, the oil obtained was stirred up with a little diethyl ether and the crystallizate obtained was filtered off with suction to give 19.8 g. (68% of theory) 4,4-dimethyl-1,2,3,4-tetrahydroquinolin-2-one; m.p. 113°-115° C.

b) 24.7 g. (140 mmole) of the above product were placed in 250 ml. 80% sulphuric acid and, at 5° C., a mixture of 6.5 ml. 96% nitric acid and 30 ml. 80% sulphuric acid added dropwise thereto. After 1 hour, the reaction mixture was poured on to ice, filtered off with suction, washed with water and crystallized from isopropanol to give 24.6 g. (80% of theory) 4,4-dimethyl-6-nitro-1,2,3,4-tetrahydroquinolin-2-one; m.p. 202°-204° C.

c) 15.2 g. (69 mmole) of the above compound were hydrogenated in 300 ml. methanol in the presence of 1 g. 10% palladium on charcoal. After separating off the catalyst, the solution of the amine obtained was mixed with 25 ml. acetic anhydride, slowly evaporated in a vacuum and the residue digested with ethyl acetate and filtered off with suction to give 15.1 g. (94% of theory) 4,4-dimethyl-6-acetylamino-1,2,3,4-tetrahydroquinolin-2-one.

d) 15 g. (65 mmole) of the above acetamide were mixed dropwise in 100 ml. 90% sulphuric acid at 5° C. with 3 ml. 96% nitric acid. After 30 minutes at 25° C., the reaction mixture was poured on to ice, filtered off with suction and washed with water to give 14.6 g. (82%. of theory) 4,4-dimethyl-6-acetylamino-7-nitro-1,2,3,4-tetrahydroquinolin-2-one; m.p. 272°-278° C.

e) 14.2 g. (51.3 mmole) of the above compound were boiled in 150 ml. ethanol and 30 ml. concentrated hydrochloric acid for 8 hours. The reaction mixture was diluted to the double volume with water, filtered off with suction and then washed with water to give 9.7 g. (80% of theory) 4,4-dimethyl-6-amino-7-nitro-1,2,3,4-tetrahydroquinolin-2-one; m.p. 313°-317° C.

f) 4.7 g. (20 mmole) of the above compound were mixed in 50 ml. pyridine, while cooling with ice, with 3.7 g. (22 mmole) 4-methoxybenzoyl chloride. After 2 hours at 25° C., the reaction mixture was poured on to ice, acidified with 2N hydrochloric acid, extracted with methylene chloride, dried and evaporated to give 6.9 g. (93% of theory) 4,4-dimethyl-6-(4-methoxybenzoylamino)-7-nitro- 1,2,3,4-tetrahydroquinolin-2-one; m.p. 288°-290° C.

EXAMPLE 5

8,8-Dimethyl-2-(4-pyridyl)-5,6,7,8-tetrahydro-1H-imidazo[4,5-g]quinolin-6-one

Analogously to Example 4, the title compound was obtained in a yield of 72% of theory; m.p. 201°-202° C.

EXAMPLE 6

2-(4-Pyridyl)-5,6,7,8-tetrahydro-1H-imidazo[4,5-g]-quinolin-6-one 2.4 g. (7.7 mmole) 6-isonicotinoylamino-7-nitro-1,2,3,4-tetrahydroquinolin-2-one were hydrogenated in 100 ml. methanol in the presence of 0.4 g. 10% palladium on charcoal. After filtering off the catalyst and evaporating the filtrate, the residue was boiled for 24 hours with 80 ml. ethanol and 15 ml. concentrated hydrochloric acid. The evaporation residue was treated with water and ammonia, filtered off with suction and recrystallized from methanol to give 1.3 g. (62% of theory) of the title compound; m.p. above 300° C.

The starting material was prepared as follows: a) 37 g. (250 mmole) 1,2,3,4-tetrahydroquinolin-2-one were nitrated in 100 ml. concentrated sulphuric acid at 0° to 5° C. with nitration acid (17.3 g. 96% nitric acid 30 g. concentrated sulphuric acid). After the dropwise addition, the reaction mixture was further stirred for 5 minutes, poured on to ice, filtered off with suction and well washed with water to give 30 g. (62% of theory) 6-nitro-1,2,3,4-tetrahydroquinolin-2-one; m.p. 202°-204° C.

b) 30 g. (156 mmole) of the nitro compound were hydrogenated in 300 ml. methanol in the presence of 3 g. 10% palladium on charcoal. After filtering off the catalyst and evaporating the solvent, there were obtained 25 g. (98% of theory) 6-amino-1,2,3,4-tetrahydroquinolin-2-one;
m.p. 178°-181° C.

c) 13.9 g. (85.7 mmole) of the amine were acylated with 16.8 g. (94.3 mmole) isonicotinic acid chloride hydrochloride and 26.3 ml. triethylamine in 200 ml. methylene chloride. The evaporation residue was worked up with water, filtered off with suction and dried to give 22 g. (98% of theory) 6-isonicotinoylamino-1,2,3,4-tetrahydro quinolin-2-one; m.p. 232°-234° C.

d) 22.7 g. (85 mmole) of the above amide were slowly introduced at 5° C. into 120 ml. 65% nitric acid. The reaction mixture was further stirred at 25° C. for 1 hour, poured on to ice and filtered off with suction. The residue was purified over silica gel (elution agent: methylene chloride/methanol saturated with ammonia; 95:5 v/v) to give 2.4 g. (10% of theory) 6-isonicotinoylamino-7-nitro-1,2,3,4-tetrahydroquinolin-2-one; m.p. 285°-288° C.

EXAMPLE 7

8,8-Dimethyl-2-(4-pyridyl)-5,6,7,8-tetrahydro-1H-imidazo[4,5-g]isoquinolin-5-one 5 g. (20.4 mmole) 4,4-dimethyl-6-nitro-7-amino-1,2,3,4-tetrahydroisoquinolin-1-one were hydrogenated in 120 ml. methanol in the presence of 0.5 g. 10% palladium on charcoal. After separating off the catalyst, the evaporation residue (4.3 g.) was acylated in 150 ml. methylene chloride and 8.4 ml. triethylamine with 5.4 g. isonicotinic acid chloride hydrochloride. After 1 hour, the evaporation residue is worked up with water and filtered off with suction. The moist residue was subsequently boiled in 100 ml. ethanol and 20 ml. concentrated hydrochloric acid for 24 hours, evaporated, mixed with water and neutralized. After column chromatography (silica gel, elution agent: methylene chloride/methanol saturated with ammonia; 15:1 v/v) and boiling up, there were obtained 2.3 g. (41% of theory) of the title compound; m.p. above 300° C.

The starting material was prepared as follows:

a) 44.5 g. (240.5 mmole) 4,4-dimethyl-1,2,3,4-tetrahydroisoquinolin-1-one (J. Het. Chem., 7, 615/1970) in 200 ml. concentrated sulphuric acid were nitrated dropwise at −10° to 0° C. with 10.5 ml. 96% nitric acid. Subsequently, the reaction mixture was poured on to ice, filtered off with suction, then washed with water and the dried residue purified over silica gel (elution agent: methylene chloride/ethyl acetate; 2:1 v/v) to give 47 g. (85% of theory) 4,4-dimethyl-7-nitro-1,2,3,4-tetrahydroisoquinolin-1-one; m.p. 227°-230° C.

b) 47 g. (204 mmole) of the above compound were hydrogenated in 1000 ml. methanol in the presence of 3 g. 10% palladium on charcoal, subsequently filtered off from the catalyst and the residue of the evaporated filtrate suspended in 300 ml. ethyl acetate and mixed with 30 ml. acetic anhydride. After 30 minutes, the product was filtered off with suction and washed with ethyl acetate to give 46.7 g. (94% of theory) 4,4-dimethyl-7-acetylamino-1,3,4-tetrahydro-isoquinolin-1-one; m.p. 250°-251° C.

c) 45 g. (186 mmole) of the above compound were nitrated in 300 ml. concentrated sulphuric acid at 0° C. by dropping in nitration acid (8.5 ml. 96% nitric acid + 30 ml. concentrated sulphuric acid). After completion of the addition, the reaction mixture was further stirred for 3 hours at 25° C., poured on to ice, filtered off with suction and recrystallized from 400 ml. glacial acetic acid. The crystallizate contained the false isomer (24 g.). The filtrate was evaporated and the residue boiled with 200 ml. ethanol and 40 ml. concentrated hydrochloric acid for 20 hours, evaporated, mixed with water, neutralized, extracted with methylene chloride, dried and evaporated. The residue was purified by column chromatography (silica gel, elution agent: ethyl acetate/-methylene chloride; 1:10 v/v to 1:1 v/v) to give 11 g. (25% of theory) 4,4-dimethyl-6-nitro-7-amino-1,2,3,4-tetrahydroisoquinolin-1-one; m.p. 231°-234° C.

EXAMPLE 8

8,8-Dimethyl-2-(4-pyridyl)-5,6,7,8-tetrahydro-1H-imidazo-[4,5-g]isoquinoline-5,7-dione 27 g. (82 mmole) 4,4-dimethyl-6-nitro-7-amino-8-bromo-1,2,3,4-tetrahydroisoquinoline-1,3-dione were hydrogenated in 300 ml. methanol in the presence of 2 g. 10% palladium on charcoal. After separating off the catalyst, the filtrate was evaporated, the residue was mixed with 500 ml. methylene chloride and 50 ml. triethylamine and, while cooling, 24 g. isonicotinic acid chloride hydrochloride slowly introduced. After 4 hours, the methylene chloride was evaporated off, the residue was worked up with water, filtered off with suction and the moist residue heated under reflux for 20 hours in 500 ml. ethanol and 200 ml. concentrated hydrochloric acid. The evaporation residue was subsequently mixed with water, neutralized and purified by column chromatography (silica gel, elution agent: methylene chloride/ methanol saturated with ammonia; 10:1 v/v). After recrystallization from ethanol/water, there were obtained 12.2 g. (51% of theory) of the title compound; m.p. above 300° C.

The starting material was prepared as follows: a) 45 g. (184 mmole) 4,4-dimethyl-7-acetylamino-1,2,3,4-tetrahydroisoquinoline-1,3-dione were dissolved in 165 ml. concentrated sulphuric acid and 17 ml. water, 33 g. silver sulphate were added thereto and, with ice cooling, 9.5 ml. bromine added dropwise thereto, subsequently further stirred for 30 minutes at 25° C., poured on to ice and filtered off with suction. The residue was washed with methylene chloride/methanol, the filtrate evaporated, digested with ethanol and filtered off with suction to give 42 g. (95% of theory) 4,4-dimethyl-7-acetylamino-8-bromo-1,2,3,4-tetrahydroisoquinoline-1,3-dione.

b) 42 g. (130 mmole) of the above compound were introduced at 5° C. into a mixture of 400 ml. concentrated sulphuric acid and 80 ml. 96% nitric acid. The reaction mixture was stirred for 45 minutes at 15° C., poured on to ice, filtered off with suction and washed with water to give 37 g. (77% of theory) 4,4-dimethyl-6-nitro-7-acetylamino-8-bromo-1,2,3,4-tetrahydroisoquinoline-1,3-dione.

c) 37 g. (100 mmole) of the above compound were deacetylated by refluxing for 20 hours in 350 ml. ethanol and 175 ml. concentrated hydrochloric acid. After cooling, the reaction mixture was poured on to ice, filtered off with suction and washed with water to give 27.4 g. (84% of theory) 4,4-dimethyl-6-nitro-7-amino-8-bromo-1,2,3,4-tetrahydroisoquinoline-1,3-dione; m.p. 218°–221° C.

EXAMPLE 9

8,8-Dimethyl-7-hydroxy-2-(4-pyridyl)-5,6,7,8-tetrahydro-1H-imidazo[4,5-g]isoquinolin-5-one 5 g. (17 mmole) of the compound obtained in Example 8 were suspended in 250 ml. dioxan, 250 ml. methanol and 25 ml. water. While cooling with water, sodium borohydride was added thereto in 0.5 g. portions. After each addition, the course of the reaction is monitored chromatographically. When the substance had just gone into solution (conversion 70% of theory), the reaction is discontinued. The product is precipitated by the addition of 1 liter of water and evaporated to give 3.8 g. (76% of theory) of the title compound; m.p. 260°–268° C.

EXAMPLE 10

7,8-Dimethyl-2-(4-pyridyl)-5,6-dihydro-1H-imidazo-[4,5-g]isoquinolin-5-one 3.5 g. (11.4 mmole) of the compound obtained in Example 9 were introduced, with cooling, into 35 ml. concentrated sulphuric acid, stirred for 4 hours at 25° C., poured on to ice, neutralized and filtered off with suction. The residue was purified by column chromatography (elution agent: methylene chloride/methanol saturated with ammonia, 10:1 v/v) and the title compound obtained again digested in methanol and filtered off with suction to give 1.8 g. (55% of theory); m.p. above 300° C.

EXAMPLE 11

2-(4-Pyridyl)-5,6,7,8-tetrahydro-1H-imidazo[4,5-g]-quinoxaline-6,7-dione

Analogously to Example 3, from 2-(4-pyridyl)-5-amino-6-nitrobenzimidazole, by hydrogenation and reaction with diethyl oxalate, there was obtained, in a yield of 45% of theory, the title compound; m.p. above 300° C.

EXAMPLE 12

5,8-Dimethyl-2-(4-pyridyl)-5,6,7,8-tetrahydro-1H-imidazo-[4,5-g]quinoxaline-6,7-dione × HCl × H$_2$O 2.8 g. (10 mmole) 1,4-dimethyl-6,7-dinitro-1,2,3,4-tetrahydroquinoxaline-2,3-dione (J. Chem. Soc., 1170, 1962) were hydrogenated in 80 ml. ethanol in the presence of 0.28 g. platinum oxide at 5 bar and 40° C. for 16 hours. After separating off the catalyst, 1.07 g. (10 mmole) pyridine-4-aldehyde and 0.19 g. (1 mmole) p-toluenesulphonic acid were added to the filtrate and heated for 2 hours with the passing through of air. After evaporating and adding ethanolic hydrochloric acid, there was obtained 1.1 g. (36% of theory) of the title compound; m.p. 270° C. (decomp.).

EXAMPLE 13

8,8-Dimethyl-2-(3-chlorophenyl)-5,6,7,8-tetrahydro-1H-imidazo[4,5-g]quinolin-6-one a) 50 g. (0.21 mole) 4,4-dimethyl-6-amino-7-nitro1,2,3,4-tetrahydroquinolin-2-one (see Example 4e) were hydrogenated in 3000 ml. methanol in the presence of 5 g. 10% palladium on charcoal. After filtering off the catalyst and evaporating the solvent, there were obtained, after crystallization from ethanol, 35.2 g. (81% of theory) 4,4-dimethyl-6,7-diamino-1,2,3,4-tetrahydroquinolin- 2-one; m.p. 192°–194±° C.

b) 1 g. (4.8 mmole) of the above diamine was stirred with 0.92 g. (5.8 mmole) 3-chlorobenzoic acid in 10 ml. polyphosphoric acid at 160° C. for 2 hours. After dilution with ice/water, the reaction mixture was filtered with suction, the residue again suspended in water, neutralized with 2N aqueous ammonia solution and the residue filtered off with suction and recrystallized from ethanol to give 1.2 g. (76% of theory) of the title compound; m.p. 190°–193° C.

EXAMPLE 14

The following compounds are obtained in a manner analogous to that described in Example 13.

| | designation | yield % | melting point (solvent) |
|---|---|---|---|
| (a) | 8,8-dimethyl-2-(4-quinolinyl)-5,6,7,8-tetrahydro-1H-imidazo[4,5-g]quinolin-6-one as dihydrochloride | 60 | 265–268° C. (isopropanol) |
| (b) | 8,8-dimethyl-2-(4-methyl-Phenyl)-5,6,7,8-tetrahydro-1H-imidazo[4,5-g]quinolin-6-one | 84 | 205–207° C. (methanol) |
| (c) | 8,8-dimethyl-2-(2-methoxyphenyl)-5,6,7,8-tetrahydro-1H-imidazo[4,5-g]quinolin-6-one | 25 | 24014 242° C. (ethyl acetate) |
| (d) | 8,8-dimethyl-2-(4-pyridazinyl)-5,6,7,8-tetrahydro-1H-imidazo[4,5-g]quinolin-6-one | 42 | >300° C. (methanol) |
| (e) | 8,8-dimethyl-2-(2-phenylethen-1-yl)-5,6,7,8-tetra- | 15 | >300° C. (ethyl acetate) |

-continued

|   | designation | yield % | melting point (solvent) |
|---|---|---|---|
|   | hydro-1H-imidazo[4,5-g]-quinolin-6-one |   |   |
| (f) | 8,8-dimethyl-2-(1-hexyl)-5,6,7,8-tetrahydro-1H-imidazo[4,5-g]quinolin-6-one | 62 | 214–215° C. (ethyl acetate) |
| (g) | 8,8-dimethyl-2-(4-chloro-phenyl)-5,6,7,8-tetrahydro-1H-imidazo[4,5-g]quinolin-6-one | 48 | >300° C. (methanol) |

EXAMPLE 15

8,8-Dimethyl-2-(4-methoxybenzoylamino)-5,6,7,8-tetrahydroquinolin-1H-imidazo[4,5-g]quinolin-6-one a) 3 g. 1(14.6 mmole) 4,4-dimethyl-6,7-diamino-1,2,3,4-tetrahydroquinolin-2-one (see Example 13a)) were dissolved in 100 ml. ethanol, mixed with 1.7 g. (16.1 mmole) cyanogen bromide and stirred for 5 hours at 25° C. The evaporation residue was again dissolved in ethanol, cooled, concentrated to about 10 ml., acetone added thereto and then filtered with suction. There were obtained 4.25 g. (94% of theory) 8,8-dimethyl-2-amino-5,6,7,8-tetrahydro-1H-imidazo[4,5-g]quinolin-6-one in the form of its hydrobromide; m.p. >300° C.

b) 4.0 g. (12.8 mmole) of the above hydrobromide were stirred with 3.3 g. (19.2 mmole) 4-methoxybenzoyl chloride in 80 ml. pyridine for 8 hours at 50° C. The evaporation residue was suspended in water, rendered alkaline with 2N aqueous ammonia and the residue recrystallized from methanol. There were obtained 3 g. (64% of theory) of the title compound; m.p. >300° C.

EXAMPLE 16

The following compound is obtained in a manner analogous to that described in Example 15:

|   | designation | yield % | melting point (solvent) |
|---|---|---|---|
| (a) | 8,8-dimethyl-2-(4-pyridyl-carbonylamino)-5,6,7,8-tetrahydro-1H-imidazo[4,5-g]-quinolin-6-one | 80 | 230–233° C. (methanol) |

EXAMPLE 17

8,8-Dimethyl-2-hydroxy-5,6,7,8-tetrahydro-1H-imidazo-[4,5-g]quinolin-6-one 2 g. (9.7 mmole) 4,4-dimethyl-6,7-diamino-1,2,3,4-tetrahydroquinolin-2-one (see Example 13 a)) were dissolved in 50 ml. 2N hydrochloric acid and phosgene passed in for 1 hour. The evaporation residue was recrystallized from methanol to give 1.6 g. (72% of theory) of the title compound; m.p. >300° C.

EXAMPLE 18

8,8-Dimethyl-2-[4-(1H-imidazol-1-yl)-phenyl]-5,6,7,8-tetrahydro-1H-imidazo[4,5-g]quinolin-6-one 2 g. (9.7 mmole) 4,4-dimethyl-6,7-diamino-1,2,3,4-tetrahydroquinolin-2-one (see Example 13 a)), 1.67 g. (9.7 mmole) 4-(1H-imidazol-1-yl)-benzaldehyde, 0.17 g. p-toluenesulphonic acid and 120 ml. ethanol were mixed together and heated under reflux for 3 hours while passing through air. The evaporation residue was suspended in water, neutralized with 2N aqueous ammonia and recrystallized from methanol to give 1.7 g. (49% of theory) of the title compound; m.p. >300° C.

EXAMPLE 19

The following compounds are obtained in a manner analogous to that described in Example 18:

|   | designation | yield % | melting point (solvent) |
|---|---|---|---|
| (a) | 8,8-dimethyl-2-(2-methoxy-4-diethylaminophenyl)-5,6,7,8-tetrahydro-1H-imidazo-[4,5-g]quinolin-6-one | 52 | 183–185° C. (ethyl acetate) |
| (b) | 8,8-dimethyl-2-(3,4-methylene-dioxyphenyl)-5,6,7,8-tetrahydro-1H-imidazo-[4,5-g]quinolin-6-one | 35 | 200–204° C. (methanol) |
| (c) | 8,8-dimethyl-2-(4-diethyl-aminophenyl)-5,6,7,8-tetrahydro-1H-imidazo[4,5-g]-quinolin-6-one × toluene-sulphonic acid | 63 | 320–321° C. (methanol/ethyl acetate) |
| (d) | 8,8-dimethyl-2-(4-diethyl-amino-2-allyloxyphenyl)-5,6,7,8-tetrahydro-1H-imidazo[4,5-g]quinolin-6-one | 47 | 185–186° C. (methanol) |

EXAMPLE 20

8,8-Dimethyl-2-(3-methyl-1H-pyrazol-5-yl)-5,6,7,8-tetrahydro-1H-imidazo[4,5-g]quinolin-6-one 1.5 g. (13.6 mmole) 3-methyl-1H-pyrazole-5-aldehyde was stirred with 4.5 g. sodium hydrogen sulphite in 9 ml. water for 3 hours at 60° C. The evaporation residue was stirred with 2.79 g. (13.6 mmole) 4,4-dimethyl-6,7-diamino-1,2,3,4-tetrahydroquinolin-2-one and 40 ml. ethanol for 3 hours at 60° C. while passing through air. Half of the ethanol was distilled off, water was added and the residue was filtered off with suction and recrystallized from ethyl acetate/methanol to give 3.3 g. (82.5% of theory) of the title compound; m.p. 242°–245° C.

EXAMPLE 21

The following compounds are obtained in a manner analogous to that described in Example 20:

|   | designation | yield % | melting point (solvent) |
|---|---|---|---|
| (a) | 8,8-dimethyl-2-(3-hydroxy-4-methoxyphenyl)-5,6,7,8-tetrahydro-1H-imidazo[4,5-g]-quinolin-6-one | 63 | 206–211° C. (ethanol/water) |
| (b) | 8,8-dimethyl-2-(4-diethyl-amino-2-hydroxyphenyl)-5,6,7,8-tetrahydro-1H-imidazo[4,5-g]quinolin-6-one | 73 | 280–281° C. (methanol/methylene chloride) |
| (c) | 8,8-dimethyl-2-[4-(1-pyrrolidinyl)-phenyl]-5,6,7,8-tetrahydro-1H-imidazo-[4,5-g]quinolin-6-one | 61 | 220–221° C. (methanol) |
| (d) | 8,8-dimethyl-2-(4-methylthio-phenyl)-5,6,7,8-tetrahydro-1H-imidazo[4,5-g]quinolin-6-one | 69 | 325–330° C. (ethanol) |
| (e) | 8,8-dimethyl-2-(4-ethoxy-phenyl)-5,6,7,8-tetrahydro-1H-imidazo[4,5-g]quinolin-6-one | 74 | 255–259° C. (ethanol) |
| (f) | 8,8-dimethyl-2-(4-pentyloxy-phenyl)-5,6,7,8-tetrahydro-1H-imidazo[4,5-g]quinolin-6- | 82 | 251–253° C. (isopropanol) |

| designation | yield % | melting point (solvent) |
|---|---|---|
| one | | |

EXAMPLE 22

8,8-Dimethyl-2-(4-hydroxysulphonylphenyl)-5,6,7,8-tetrahydro-1H-imidazo[4,5-g]quinolin-6-one Analogously to Example 13 b), from 1.86 g. (9.1 mmole) 4,4-dimethyl-6,7-diamino-1,2,3,4-tetrahydroquinolin-2-one and 2.5 g. (9.2 mmole) 4-(4-morpholinosulphonyl)-benzoic acid in polyphosphoric acid at 160° C. were obtained 3 g. (91% of theory) of the title compound; m.p. >300° C., after recrystallization from methanol.

EXAMPLE 23

2,8,8-Trimethyl-5,6,7,8-tetrahydro-1H-imidazo-[4,5--g]quinolin-6-one 3.1 g. 6,7-diamino-4,4-dimethyl-1,2,3,4-tetrahydroquinolin-2-one and 2.8 ml. acetic anhydride were stirred in 50 ml. ethanol for 30 minutes at ambient temperature. 20 ml. concentrated hydrochloric acid were then added thereto and the reaction mixture refluxed for 18 hours. The solvent was removed in a vacuum and the residue was dissolved in water, rendered alkaline with ammonia, filtered off with suction and washed with water. After recrystallization from ethyl acetate, there were obtained 2.4 g. of the title compound; m.p. 290°-294° C.

EXAMPLE 24

8,8-Dimethyl-2-phenyl-5,6,7,8-tetrahydro-1H-imidazo-[4,5-g]quinolin-6-one 3.0 g. 6,7-diamino-4,4-dimethyl-1,2,3,4-tetrahydroquinolin-2-one and 1.5 ml. benzaldehyde were stirred for 20 hours in 50 ml. ethanol and 5 ml. glacial acetic acid. Half of the solvent was removed in a vacuum and the remainder was mixed with 50 ml. water and filtered off with suction. After recrystallization from ethyl acetate, there were obtained 2.4 g. of the title compound; pound; m.p. 296°-298° C.

EXAMPLE 25

The following compounds are obtained in a manner analogous to that described in Example 24:

| | designation | yield % | melting point (solvent) |
|---|---|---|---|
| (a) | 8,8-dimethyl-2-(2-thienyl)-5,6,7,8-tetrahydro-1H-imidazo[4,5-g]quinolin-6-one | 51 | >300° C. (ethanol) |
| (b) | 8,8-dimethyl-2-(2-allyloxy-phenyl)-5,6,7,8-tetrahydro-1H-imidazo[4,5-g]quinolin-6-one | 23 | 233-235° C. purification on silica gel (methylene chloride/methanolic ammonia, 98:2 v/v) |

EXAMPLE 26

8,8-Dimethyl-2-(4-cyanophenyl)-5,6,7,8-tetrahydro-1H-imidazo[4,5-g]quinolin-6-one 4.1 g. 4,4-dimethyl-6,7-diamino-1,2,3,4-tetrahydroquinolin-2-one and 2.6 g. 4-cyanobenzaldehyde were stirred in 100 ml. ethanol for 7 days at 25° C. with the action of air. Subsequently, the reaction mixture was evaporated to 10 ml., mixed with 10 ml. water, filtered off with suction and recrystallized from ethanol/water (1:1 v/v) to give 5 g. of the title compound; m.p. 228°-233° C.

EXAMPLE 27

8,8-Dimethyl-2-(4-aminocarbonylphenyl)-5,6,7,8-tetrahydro-1H-imidazo[4,5-g]quinolin-6-one 3.6 g. of the compound obtained in Example 26 were introduced into 70 ml. concentrated sulphuric acid and stirred for 24 hours at 25° C. Subsequently, the reaction mixture was poured on to ice, neutralized with a concentrated aqueous solution of ammonia, filtered off with suction and well washed with water to give 1.8 g. of the title compound which, after crystallization from ethanol/water, had a melting point of 317°-319° C.

EXAMPLE 28

8,8-Dimethyl-2-(4-pyridyl)-5,6,7,8-tetrahydro-1H-imidazo-[4,5-g]quinoline dihydrochloride 2.5 g. (8.5 mmole) 8,8-dimethyl-2-(4-pyridyl)-5,6,7,8-tetrahydro-1H-imidazo[4,5-g]quinolin-6-one (see Example 5) were slowly introduced into a suspension of 4.3 g. lithium aluminium hydride in 150 ml. tetrahydrofuran and heated under reflux for 8 hours. After decomposition of excess lithium aluminium hydride with a saturated aqueous solution of sodium chloride, extraction was carried out 3 times with methylene chloride/methanol (99:1 v/v). The evaporation residue was purified on silica gel (elution agent: methylene chloride/5% methanol), the desired fractions were evaporated and the residue dissolved in isopropanol, acidified with ethanolic hydrochloric acid and the crystals obtained filtered off with suction to give 1.0 g. of the title compound as its dihydrochloride; m.p. 240°-242° C.

EXAMPLE 29

8,8-Dimethyl-2-(4-diethylamino-2-propyloxyphenyl)-5,6,7,8-tetrahydro-1H-imidazo[4,5-g]quinolin-6-one 2 g. 8,8-Dimethyl-2-(4-diethylamino-2-allyloxyphenyl)-5,6,7,8-tetrahydro-1H-imidazo[4,5-g]quinolin-6one were hydrogenated in ethanol in the presence of palladium/charcoal. After completion of the take up of hydrogen, the catalyst was filtered off, the filtration was evaporated and the residue recrystallized from isopropanol to give 1.8 g. of the title compound; m.p. 147°-148° C.

EXAMPLE 30

The following compounds are obtained in a manner analogous to that described in Example 26:

| | designation | yield % | melting point (solvent) |
|---|---|---|---|
| (a) | 8,8-dimethyl-2-phenylmethyl-5,6,7,8-tetrahydro-1H-imidazo[4,5-g]quinolin-6-one | 65 | 293-303° C. (ethyl acetate) |
| (b) | 8,8-dimethyl-2-(4-trifluoro- | 58 | 325-330° C. |

-continued

| | designation | yield % | melting point (solvent) |
|---|---|---|---|
| | methylphenyl)-5,6,7,8-tetrahydro-1H-imidazo[4,5-g]-quinolin-6-one | | (after column chromatography) |
| (c) | 8,8-dimethyl-2-(1-naphthyl)-5,6,7,8-tetrahydro-1H-imidazo[4,5-g]quinolin-6-one | 68 | 212–220° C. (after column chromatography) |
| (d) | 8,8-dimethyl-2-(4-hydroxyphenyl)-5,6,7,8-tetrahydro-1H-imidazo[4,5-g]quinolin-6-one | 49 | 245–249° C. (after column chromatography) |
| (e) | 8,8-dimethyl-2-(3-hydroxyphenyl)-5,6,7,8-tetrahydro-1H-imidazo[4,5-g]quinolin-6-one | 63 | 335–340° C. (ethyl acetate) |
| (f) | 8,8-dimethyl-2-(4-tert.-butyl-phenyl)-5,6,7,8-tetrahydro-1H-imidazo[4,5-g]quinolin-6-one | 72 | 345–347° C. |
| (g) | 8,8-dimethyl-2-(2-furyl)-5,6,7,8-tetrahydro-1H-imidazo-[4,5-g]quinolin-6-one | 46 | >300° C. (ethanol) |
| (h) | 8,8-dimethyl-2-(2-methyl-3-hydroxy-5-hydroxymethyl-pyridin-4-yl)-5,6,7,8-tetrahydro-1H-imidazo[4,5-g]-quinolin-6-one | 48 | >300° C. (methanol/water) |
| (i) | 8,8-dimethyl-2-(4-nitrophenyl)-5,6,7,8-tetrahydro-1H-imidazo[4,5-g]quinolin-6-one | 92 | 352–357° C. (ethanol/5% water) |

EXAMPLE 31

8,8-Dimethyl-2-(4-chloro-2-methoxyphenyl)-5,6,7,8-tetrahydro-1H-imidazo[4,5-g]quinolin-6-one In a manner analogous to that described in EXAMPLE 2, from 4-chloro-2-methoxybenzoyl chloride and 4,4-dimethyl-6,7-diamino-1,2,3,4-tetrahydroquinolin-2-one (see Example 13 a)), after column chromatography, there was obtained a yield of 58% of theory of the title compound; m.p. 300°–303° C.

EXAMPLE 32

8,8-Dimethyl-2-(2-indolyl)-5,6,7,8-tetrahydro-1H-imidazo-[4,5-g]quinolin-6-one

In a manner analogous to that described in Example 2, from indole-2-carboxylic acid chloride and 4,4-dimethyl-6,7-diamino-1,2,3,4-tetrahydroquinolin-2-one (see Example 13 a)), after column chromatography, there was obtained a yield of 45% of theory of the title compound; m.p. 264°–267° C.

EXAMPLE 33

8,8-Dimethyl-2-(4-methylsulphonyl)-5,6,7,8-tetrahydro-1H-imidazo[4,5-g]quinolin-6-one 3.6 g. (11 mmol) 8,8-dimethyl-2-(4-methylthiophenyl)- 5,6,7,8-tetrahydro-1H-imidazo[4,5-g]quinolin-6-one (see Example 21 d)) were stirred in 40 ml. glacial acetic acid with 7.2 ml. hydrogen peroxide for 3 days at 25° C. Subsequently, the reaction mixture was concentrated to 10 ml., mixed with diethyl ether, filtered off with suction and purified by column chromatography (elution agent: methylene chloride/methanol/glacial acetic acid; 30:1:0.1 v/v/v). The residue of the evaporated fractions was suspended in water, rendered ammoniacal, filtered off with suction and washed with water to give 2.4 g. (59% of theory) of the title compound; m.p. 219°–222° C.

EXAMPLE 34

8,8-Dimethyl-2-(4-methylsulphonyloxyphenyl)-5,6,7,8-tetrahydro-1H-imidazo[4,5-g]quinolin-6-one 2 g. (6.5 mmole) 8,8-dimethyl-2-(4-hydroxyphenyl)-5,6,7,8-tetrahydro-1H-imidazo[4,5-g]quinolin-6-one (see Example 30 d)) were suspended in 10 ml. water and, while cooling with ice, 5 ml. (65 mmole) methanesulphonic acid chloride and 50 ml. 2N aqueous sodium hydroxide solution were alternatingly added dropwise thereto in such a manner that a pH value of about 10 to 13 was always present. When the reaction was completed, the reaction mixture was filtered off with suction, the product was washed with water and purified by column chromatography (elution agent: methylene chloride/ methanol/acetic acid; 10:1:0.2 v/v/v). The evaporation fractions were suspended in water, rendered ammoniacal and washed with water to give 1.5 g. (68% of theory) of the title compound; m.p. 209°–215° C.

EXAMPLE 35

8,8-Dimethyl-2-(4-propylsulphonyloxyphenyl)-5,6,7,8-tetrahydro-1H-imidazo[4,5-g]quinolin-6-one In a manner analogous to that described in Example 34, from 2 g. (6.5 mmole) 8,8-dimethyl-2-(4-hydroxyphenyl)-5,6,7,8-tetrahydro-1H-imidazo[4,5-g]-quinolin-6-one and 7.3 ml. (65 mmole) 1-propanesulphonic acid chloride, there was obtained 1.5 g. (56% of theory) of the title compound; m.p. 148°–156° C.

EXAMPLE 36

8,8-Dimethyl-2-(4-carboxyphenyl)-5,6,7,8-tetrahydro-1H-imidazo[4,5-g]quinolin-6-one 6.8 g. (21.5 mmole) 8,8-dimethyl-2-(4-cyanophenyl)-5,6,7,8-tetrahydro-1H-imidazo[4,5-g]quinolin-6-one (see Example 26) were heated under reflux for 2 days with 14 g. potassium hydroxide in 100 ml. ethanol, subsequently evaporated in a vacuum and the residue taken up in water and acidified with concentrated hydrochloric acid to give 7.4 g. of the title compound in the form of a yellow, amorphous powder.

EXAMPLE 37

8,8-Dimethyl-2-(4-hydroxymethylphenyl)-5,6,7,8-tetrahydro-1H-imidazo[4,5-g]quinolin-6-one 3.35 g. (10 mmole) 8,8-dimethyl-2-(4-carboxyphenyl)-5,6,7,8-tetrahydro-1H-imidazo[4,5-g]quinolin-6-one (see Example 36) were dissolved in 100 ml. dimethylformamide and, after the removal of entrained water, concentrated to 50 ml. After the dropwise addition of 1.4 ml. triethylamine, 0.95 ml. ethyl chloroformate was added dropwise at 0 to 5° C. Into this solution was added dropwise at 5 to 10° C. 1 g. sodium borohydride dissolved in 30 ml. dimethylformamide. After distilling off the dimethylformamide, the residue was mixed with water, acidified with 2N hydrochloric acid, filtered off with suction and purified by column chromatography (elution agent: methylene chloride/methanol saturated with ammonia; 10:1 v/v). After crystallization from ethanol, there were obtained 0.8 g. (25% of theory) of the title compound; m.p. 214°–232° C.

EXAMPLE 38

8,8-Dimethyl-2-(4-aminophenyl)-5,6,7,8-tetrahydro-1H-imidazo[4,5-g]quinolin-6-one 13 g. 8,8-dimethyl-2-(4-nitrophenyl)-5,6,7,8-tetrahydro-1H-imidazo[4,5-g]quinolin-6-one (see Example 30*i*)) were hydrogenated in methanol in the presence of palladium/charcoal. After filtering off the catalyst, the filtrate was evaporated and the residue recrystallized from 2N hydrochloric acid/ethanol (1:1 v/v) to give 7.8 g. of the title compound in the form of its hydrochloride; m.p. 305°-308° C. (decomp.).

EXAMPLE 39

8,8-Dimethyl-2-[4-(1-pyrrolyl)-phenyl]-5,6,7,8-tetrahydro-1H-imidazo[4,5-g]quinolin-6-one 3.06 g. 8,8-dimethyl-2-(4-aminophenyl)-5,6,7,8-tetrahydro-1H-imidazo[4,5-g]quinolin-6-one (see Example 38) were allowed to stand for 20 hours at 25° C. with 30 ml. glacial acetic acid, 5 ml. water, 2 drops of concentrated hydrochloric acid and 1.32 ml. 2,5-dimethoxytetrahydrofuran. The reaction mixture was then washed with 100 ml. water. After crystallization from ethanol, there was obtained 0.8 g. of the title compound; m.p. 329°-350° C. (decomp.).

EXAMPLE 40

8,8-Dimethyl-2-(4-methoxyphenylamino)-5,6,7,8-tetrahydro-1H-imidazo[4,5-g]quinolin-6-one a) 2.7 g. (10 mmole) 1,1-dichloro-1,1-diphenoxymethane were placed in 30 ml. methylene chloride together with 2.8 ml. (20 mmole) triethylamine and, while cooling with ice, 1.2 g. (10 mmole) p-anisidine, dissolved in 10 ml. methylene chloride, added dropwise thereto. After 1 hour at 25° C., the reaction mixture was mixed with water and the organic phase was washed twice with water, dried and evaporated to give 2.9 g. (91% of theory) N-(4-methoxyphenyl)-diphenoxyimidocarbonate.

b) 2.9 g. (10 mmole) N-(4-methoxyphenyl)-diphenoxyimidocarbonate and 2.0 g. (10 mmole) 4,4-dimethyl-6,7-diamino-1,2,3,4-tetrahydroquinolin-2-one (see Example 13*a*)) were stirred in 100 ml. isopropanol for 10 hours at 70° C. After evaporating off the solvent, the residue was purified by column chromatography (elution agent: methylene chloride/methanol; 50:1 v/v to 20:1 v/v) to give 2.4 g. (72% of theory) of the title compound; m.p. 283°-287° C.

It will be understood that the specification and examples are illustrative but not limitative of the present invention and that other embodiments within the spirit and scope of the invention will suggest themselves to those skilled in the art.

EXPERIMENTAL PROTOCOL

A representative example of the compounds claimed in the application were investigated for their rheological and hemodynamic properties.

1. Protocol of the Investigations relating to Hemodynamics

As hemodynamic parameters, the average arterial pressure, the heart rate and $dp/dt_{max}$ (the derivative of the pressure in the left ventricle as a function of time—a measure of the force of the myocardial contraction) were determined. Normotonic Sprague-Dawley rats were anesthetized with inactin i.p. The animals were provided with a tracheotomy tube to facilitate spontaneous respiration. A Miller-Mikro-Tip ® was placed in the left ventricle to record the left ventricular pressure (LVP) and the $dp/dt_{max}$ was determined with the help of a computer. The vena jugularis served as i.v. access. The arterial pressure was measured by means of a catheter and a pressure transducer by way of the femoral artery. The EKG and the heart rate were derived from subcutaneous puncture electrodes.

For screening of potential cardiotonics, the doses were fractionated and applied cumulatively from 0.01 to 3.0 mg/kg at 10 minute intervals.

All substances mentioned have only a weakly positive inotropic effect. The $ED_{+1.5}$ mHg/sec (=the effective dose, which increases the control value by 1.5 mHg/sec) is higher than 3 mg/kg. Table 1 shows the behavior of the average arterial pressure and of the heart rate. The initial (control) values are compared with the values at a dose of 1 mg/kg.

2. Erythrocyte Aggregation as a Parameter of Hemorheology:

The erythrocyte aggregation was determined with the Mini-Erythrocyte Aggregometer of the Myrenne company, Roetgen [1]. As a measure of the aggregation, this instrument gives out a dimensionless index, which increases with an increasing tendency to aggregate.

All investigations were carried out with human blood of healthy donors. The blood, which was adjusted to a hematocrit of 45%, was incubated with a control solution or the substance solutions and the erythrocyte aggregation was subsequently measured. Each substance was investigated at a concentration of $10^{-6}$M and $10^{-5}$M. Two experiments with the blood of different donors were carried out per substance. The difference between the aggregation indices of the initial value of the control solution and the values with the substance solution were calculated.

The present findings with respect to the erythrocyte aggregation of the above-mentioned substances are listed in Table 2. The lower the value listed, the more effective is the substance.

On the other hand, Venoruton ®, a mixture of different O-(beta-hydroxyethyl)rutosides, at a comparable concentration of $1.7 \times 10^{-5}$, merely brings about a decrease in the erythrocyte aggregation index by 0.4. Even at concentration of $1.7 \times 10^{-3}$M, the reduction in the erythrocyte concentration is only $3.9 \pm 0.9$. Venoruton ® is said to inhibit the tendency of erythrocytes to aggregate [2]. In comparison to Venoruton ®, the BM substances named clearly reduce the erythrocyte aggregation more.

References

1. Kiesewetter, H. et al. The Mini Erythrocyte Aggregometer, a New Instrument for Rapidly Quantifying the Extent of the Erythrocyte Aggregation Biomed. Technik 27 (9) 209-213 1(1982)
2. Schmid-Schoenbein, H. et al. Effect of O-(beta-Hydroxyethyl)-Rutosides on the microrheology of human blood flow under defined flow conditions VASA 4 263-270 (1975)

TABLE 1

| Substance Example | Average arterial blood Pressure p heart rate HF The values listed are average values | | | |
|---|---|---|---|---|
| | Control | | Dose 1 mg/kg | |
| | p | HF | p | HF |
| 3 | 130 | 380 | 120 | 360 |

TABLE 1-continued

| | Average arterial blood Pressure p heart rate HF The values listed are average values | | | |
|---|---|---|---|---|
| Substance | Control | | Dose 1 mg/kg | |
| Example | p | HF | p | HF |
| 4 | 143 | 369 | 122 | 345 |
| 5 | 122 | 365 | 107 | 366 |
| 10 | 120 | 362 | 116 | 365 |
| 11 | 123 | 345 | 103 | 333 |
| 12 | 131 | 350 | 128 | 340 |

TABLE 2

Erythrocyte aggregation
in vitro Incubation of human blood (45% hematocrit)
Control K contains the respective solvent
Difference from control value is given as $\Delta K$

| Substance Example | $\Delta K$ with $c = 10^{-6}$ M | $\Delta K$ with $c = 10^{-5}$ M | $\Delta K$ with $c = 1.7 \times 10^{-5}$ M |
|---|---|---|---|
| 3 | −0.3 | −1.4 | |
| 4 | −1.4 | −8.1 | |
| 5 | −0.7 | −7.5 | |
| 8 | −1.3 | −1.8 | |
| 12 | −0.8 | −0.2 | |
| Venoruton | | | −0.4 |

We claim:

1. A tricyclic benzimidazole compound of the formula:

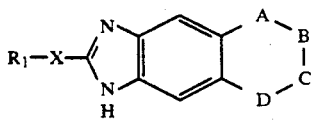

(I)

wherein $R_1$ is a phenyl of the formula:

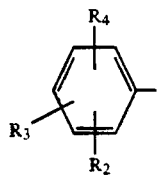

(II)

wherein $R_2$, $R_3$ and $R_4$ can be the same or different and each is hydrogen, alkylsulphonyloxy, carbonyl substituted by hydroxyl or amino, alkylthio, alkylsulphhonyl, nitro, halogen, amino, hydroxyl, alkyl, alkoxy, alkenyloxy, hydroxyalkyl, dialkylamino, 1-imidazoyl, trifluoromethyl, cyano, hydroxy-sulphonyl, 1-pyrrolidino or pyrrolyl and wherein the phenyl carries 1-3 of the above substituents, or $R_1$ is naphthyl or methylenedioxyphenyl or a five- or six-membered heterocyclic ring selected from the group consisting of pyrrole, furan, thiophene, pyrazole, pyridazine, or pyridine, which are unsubstituted or substituted at least once by alkyl or hydroxy and can be optionally condensed with a phenyl ring to form a bicyclic radical or when X is a valency bond, besides the above-mentioned groups $R_1$ can also be alkyl, hydroxyl or amino, wherein the alkyl groups are $C_1-C_{10}$ straight or branched chains, X is a valency bond, $C_1-C_4$ alkylene or vinylene, imino or amide (—CONH—) and A and B are carbon and either C or D is nitrogen and the other is carbon which can be substituted by hydrogen or alkyl or cycloalkyl wherein the carbon can also carry hydroxyl or oxo groups or can be components of a 3 to 7-membered spirocycle wherein the six-membered ring containing A, B, C and D can be saturated or unsaturated, the tautomers thereof and the physiologically acceptable salts thereof with inorganic and organic acids together with the optically active compounds and racemates.

2. The compound of claim 1 wherein when $R_1$ is phenyl of formula II, the alkyl of the $R_2$, $R_3$ and $R_4$ substituents are straight-chain or branched moieties.

3. The compound of claim 1 wherein when $R_1$ is phenyl of formula II, the alkyl of the $R_2$ $R_3$ and $R_4$ substituents are straight chain or branched 1–4 carbon moieties.

4. The compound of claim 1 wherein $R_1$ is phenyl of formula II, the $R_2$ and $R_4$ substituents are selected from the group consisting of methanesulphenyloxy, ethanesulphonyloxy, n-propanesulphonyloxy, isopropanesulphonyloxy, acetylamino, propionylamino, allyloxy, but-2-enyloxy, but-3-enyloxy, pent-2-enyloxy, hydroxymethyl, methylthio, ethylthio, methylsulphonyl and ethylsulphonyl.

5. The compound of claim 1 wherein when $R_1$ is phenyl of formula II, the $R_2$, $R_3$ or $R_4$ substituents wherein $R_2$ $R_3$ or $R_4$ are pyrrolidine.

6. The compound of claim 1 wherein $R_1$ is a phenyl of formula I and wherein $R_2$ is hydrogen, alkylsulphonyloxy, a carbonyl group substituted by hydroxy, amino each of the above alkyl moieties containing 1 or 2 carbon atoms, a $C_1-C_4$ nitro or cyano group alkylthio, alkylsulphonyl, each of the above alkyl moieties containing 1 or 2 carbon atoms, a halogen atom, an amino or hydroxyl group, a dialkylamino, alkyl, alkoxy, alkenyloxy group containing up to 3 carbon atoms, trifluoromethyl or 1-iomidazolyl, $R_3$ is hydrogen, an alkyl of 1-3 carbons, alkoxy or dialkylamino containing 1 or 2 carbon atoms in each alkyl moiety or a halogen atom and $R_4$ is hydrogen or methoxy.

7. The compound of claim 1, wherein $R_1$ is phenyl of formula II, wherein $R_2$ is hydrogen or a methanesulphonyloxy, aminocarbonyl, acetylamino, methylthio, methylsulphonyl, hydroxyl, methyl, methoxy, cyano, chloro, nitro, amino, dimethylamino, trifluoromethyl or 1-imidazolyl, $R_3$ is hydrogen or chlorine or methyl, methoxy, dimethylamino or diethylamino, $R_4$ is hydrogen or methoxy or $R_1$ is pyrrole, furan, thiophene, pyrazole, pyridine, pyridazine or a methyl-, ethyl-, substituted derivative thereof or a naphthalene, indole, indazole, quinoline or isoquinoline radical or, X is a valency bond, methylene or vinylene or an imino or amido and A, B, C and D signify one nitrogen atom, the others representing carbon atoms which can be substituted by hydrogen or methyl and the carbon atoms can additionally also carry hydroxyl or oxo or can be components of a spirocycle with 5 carbons.

8. The compound of claim 1, wherein $R_1$ is phenyl optionally substituted by methoxy, ethoxy, chlorine, methyl, hydroxy, dimethylamino, diethylamino, imidazol-1-yl, allyloxy, cyano or aminocarbonyl, methylenedioxyphenyl or a pyridyl, quinolinyl, pyridazinyl, pyrazolyl or thienyl or a methyl-substituted derivative thereof or, when X is a valency bond, besides the above groups, $R_1$ is methyl, n-hexyl or hydroxyl.

9. The compound of claim 1, wherein when $R_1$ is monosubstituted phenyl the substituents in the 2-, 3- or 4-position are selected from the group consisting of hydroxyl, $C_1$-$C_3$-alkyl, $C_1$-$C_3$-alkoxy, allyloxy, halo-, nitro, cyano, aminocarbonyl, amino, $C_1$-$C_3$-dialkylamino, $C_1$-$C_3$-alkylthio, $C_1$-$C_3$-alkylsulphonyl, $C_1$-$C_3$-alkylsulphonyloxy and 1-imidazolyl.

10. The compound of claim 1 wherein when $R_1$ is disubstituted phenyl the substituents are selected from the group consisting of alkanesulphonyloxy, carbonyl substituted by hydroxy or amino hydroxyl, alkyl, alkoxy, allyloxy, cyano, halo, nitro, amino, dialkylamino, alkylthio, alkylsulphonyl and 1-imidazolyl and wherein the two substituents are the same or different and are in the 2,3-, 2,4- 2,5-, 2,6-, 3,4- or 3,5-position and any of the above alkyl, alone or in combination with other radicals can contain up to 3 carbon atoms.

11. The compound of claim 6 wherein the substituents are in the 2,4-, 2,5- or 3,4- position.

12. The compound of claim 1 wherein the substituted phenyl is 3,4,5-trimethoxyphenyl.

13. The compound of claim 1 wherein the alkyl substituents in the heterocyclic five- and six-membered ring are methyl and ethyl.

14. The compound of claim 1 wherein the heterocyclic five- and six-membered ring is condensed with a phenyl ring to form cyclic compounds selected from the group consisting of indole, indazole, quinoline, isoquinoline, phthalazine, benzofuran and benzothiophene.

15. The compound of claim 1 wherein when X is a valency bond $R_1$ is selected from the group consisting of methyl, ethyl, propyl, butyl, pentyl and hexyl.

16. The compound of claim 1 wherein
A is —$CH_2$—, —$C(CH_3l)_2$—, —$C(CH_3l)$=,
B is $C(CH_3)_2$—, =CH—, —$CH_2$—, —C(O)—, —CHOH—, =$C(CH_3)$—, or
C is —C(O)—, —NH—, —$CH_2$—, and
D is —NH—, —C(O)— or —N($CH_3$)—wherein C and D cannot both be nitrogen-containing groups.

17. The compound of claim 1 wherein
A is —$C(CH_3)_2$—,
B is —$CH_2$—,
C is —C(O)— and
D is —NH—.

18. The tricyclic benzimidazole compound designated 8,8-Dimethyl-2-(4-methoxyphenyl)-5,6,7,8-tetrahydro-1H-imidazo[4,5-g]quinolin-6-one.

19. The tricyclic benzimidazole compound designated 8,8-Dimethyl-2-(4-pyridyl)-5,6,7,8-tetrahydro-1H -imidazo[4,5-g]quinolin-6-one.

20. The tricyclic benzimidazole compound designated 8,8-Dimethyl-2-(4-pyridyl)-5,6,7,8-tetrahydro-1H-imidazo[4,5-g]isoquinoline-5,7-dione.

21. The tricyclic benzimidazole compound designated 7,8-Dimethyl-2-(4-pyridyl)-5,6-dihydro-1H-imidazo-[4,5-g]iso-quinoline-5-one.

22. A pharmaceutical composition for the treatment and inhibition of the aggregation of thrombocytes and erythrocytes, to lower blood pressure and increase the power of the heart wherein said composition contains a pharmaceutically effective amount of at least one compound of claim 1 in a pharmaceutically acceptable carrier.

23. A method of treatment and inhibition of the aggregation of thrombocytes and erythrocytes, to lower blood pressure and increase the power of the heart comprising administering an effective amount of at least one of a pharmaceutically acceptable compound of claim 1.

24. The compound of claim 1, wherein the tricyclic ring system is a 2,3,5,6,7,8-hexahydro-1H-imidazo quinoline-4,6-dione, 5,6,7,8-tetrahydro-1-H-imidazo isoquinolin-5-one, 5,6-dihydro-1-H-imidazo isoquinolin-5-one, 5,6,7,8-tetrahydro-1Himidazo isoquinoline-5,7-dione, 5,6,7,8-tetrahydro-1H-imidazo-quinoline-6-one or 5,6,7,8-tetrahydro-1H-imidazo-quinoline and the methyl- or hydroxy substituted derivatives thereof.

25. A pharmaceutical composition for the treatment and inhibition of the aggregation of thrombocytes and erythrocytes, to lower blood pressure and increase the power of the heart wherein said composition contains a pharmaceutically effective amount of at least one compound selected from the group consisting of 8,8-Dimethyl-2-(4-pyridyl)5,6,7,8-tetrahydro-1-H-imidazo isoquinoline-5-one, 8,8-Dimethyl-7-hydroxy-2-(4-pyridyl)-5,6,7,8-tetrahydro-1H-imidazo isoquinoline-5-one, 8,8-Dimethyl-2-(4-methoxyphenyl)-5,6,7,8-tetrahydro-1H-imidazo quinoline-6-one, 8,8-Dimethyl-2-(4-pyridyl)-5,6,7,8-tetrahydro-1H-imidazo quinoline-6-one, 8,8-Dimethyl-2-(4-pyridyl)-5,6,7,8-tetrahydro-1H-imidazo isoquinoline-5,7-dione, 8, 8-diemthyl-2-(4-trifluoromethylphenyl) 1-H-imidazoquinoline-6-one and 7,8-Dimethyl-2-(4-pyridyl)-5,6-dihydro-1H-imidazoisoquinoline-5-one.

26. A method of treatment and inhibition of the aggregation of thrombocytes and erythrocytes, to lower blood pressure and increase the power of the heart comprising administering an effective amount of at least one of a pharmaceutically acceptable compound of claim 1 selected from the group consisting of 8,8-Dimethyl-2-(4-pyridyl)-5,6,7,8-tetrahydro-1-H-imidazo isoquinoline-5-one, 8,8-Dimethyl-7-hydroxy-2-(4-pyridyl)-5,6,7,8-tetrahydro-1H-imidazo isoquinoline-5-one, 8,8-Dimethyl-2-(4-methoxyphenyl)-5,6,7,8tetrahydro-1H-imidazo quinoline-6-one, 8,8-Dimethyl-2-(4-pyridyl)-5,6,7,8-tetrahydro-1H-imidazo quinoline-6-one, 8,8-Dimethyl-2-(4-pyridyl)-5,6,7,8-tetrahydro-1H-imidazo isoquinoline-5,7-dione, 8,8-(dimethyl-2-(4-trifluoromethylphenyl)-5,6,7,8-tetrahydro-1-H-imidazoquinoline-6-one and 7,8-Dimethyl-2-(4-pyridyl)-5,6-dihydro-1H-imidazoisoquinoline-5-on.

27. The tricyclic benzimidazole compound designated 8,8-dimethyl-2-(4-trifluormethylphenyl)-5,6,7,8-tetrahydro-1H-imidazo-quinoline-6-one.

* * * * *

UNITED STATES PATENT AND TRADEMARK OFFICE
CERTIFICATE OF CORRECTION

PATENT NO. : 5,116,843            Page 1 of 2

DATED : May 26, 1992

INVENTOR(S) : Mertens et al.

It is certified that error appears in the above-identified patent and that said Letters Patent is hereby corrected as shown below:

| | |
|---|---|
| Col. 10, line 51: | before "100°C." delete "." and insert -- + --. |
| Col. 12, line 8: | after "A," delete "8" and insert -- B --. |
| Col. 15, line 57: | after "2'-" delete "{" and insert -- ( --. |
| Col. 15, line 60: | after "2'-(" delete "Z" and insert -- 2 --. |
| Col. 16, line 11: | after "6,7" delete "dion" and insert -- -dione --. |
| Col. 17, line 19: | after "lin-8-one x" delete "H2O" and insert -- $H_2O$ --. |
| Col. 22, line 62: | in "melting point (solvent)" column after "240" delete "14" and insert -- - --. |
| Col. 23, line 17: | after "3 g." delete "1". |
| Col. 30, line 57: | after "213" delete "1". |
| Col. 31, line 49 Claim 1: | delete "alkylsulphhonyl" and insert -- alkylsulphonyl --. |

UNITED STATES PATENT AND TRADEMARK OFFICE
CERTIFICATE OF CORRECTION

PATENT NO. : 5,116,843
DATED : May 26, 1992
INVENTOR(S) : Mertens et al.

It is certified that error appears in the above-identified patent and that said Letters Patent is hereby corrected as shown below:

Col. 33, line 37
    Claim 16:     delete "$C(CH_31)_2$" and insert -- $C(CH_3)_2$ --.

Col. 33, line 37:     delete "$C(CH_31)=$" and insert -- $C(CH_3)=$ --.

Col. 34, line 55
    Claim 26:     delete "5-on" and insert -- 5-one --.

Col. 34, line 57
    Claim 27:     delete "trifluormethylphenyl" and insert -- trifluoromethylphenyl --.

Signed and Sealed this

Seventh Day of December, 1993

Attest:

BRUCE LEHMAN

*Attesting Officer*      *Commissioner of Patents and Trademarks*